US008840898B2

(12) United States Patent
Goldmakher

(10) Patent No.: US 8,840,898 B2
(45) Date of Patent: Sep. 23, 2014

(54) IMMUNOCONJUGATES TARGETING SYNDECAN-1 EXPRESSING CELLS AND USE THEREOF

(75) Inventor: Viktor S. Goldmakher, Newton, MA (US)

(73) Assignees: Biotest AG, Dreieich (DE); ImmunoGen, Inc., Waltham, MA (US)

( * ) Notice: Subject to any disclaimer, the term of this patent is extended or adjusted under 35 U.S.C. 154(b) by 1038 days.

(21) Appl. No.: 11/735,644

(22) Filed: Apr. 16, 2007

(65) Prior Publication Data
US 2007/0183971 A1    Aug. 9, 2007

Related U.S. Application Data

(62) Division of application No. 10/975,434, filed on Oct. 29, 2004.

(60) Provisional application No. 60/605,394, filed on Aug. 30, 2004.

(51) Int. Cl.
*A61K 39/395*    (2006.01)

(52) U.S. Cl.
USPC ................... 424/178.1; 424/277.1

(58) Field of Classification Search
None
See application file for complete search history.

(56) References Cited

U.S. PATENT DOCUMENTS

| | | | |
|---|---|---|---|
| 3,896,111 A | 7/1975 | Kupchan et al. | |
| 4,137,230 A | 1/1979 | Hashimoto et al. | |
| 4,151,042 A | 4/1979 | Higashide et al. | |
| 4,169,888 A | 10/1979 | Hanka et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,418,064 A | 11/1983 | Powell et al. | |
| 4,424,219 A | 1/1984 | Hashimoto et al. | |
| 4,444,887 A | 4/1984 | Hoffmann | |
| 4,761,111 A | 8/1988 | Brown | |
| 5,053,394 A | 10/1991 | Ellestad et al. | |
| 5,208,020 A * | 5/1993 | Chari et al. | 424/181.1 |
| 5,367,086 A | 11/1994 | Rao | |
| 5,475,092 A | 12/1995 | Chari et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,585,499 A | 12/1996 | Chari et al. | |
| 5,639,641 A | 6/1997 | Pedersen et al. | |
| 5,703,247 A | 12/1997 | Kingston et al. | |
| 5,705,508 A | 1/1998 | Ojima et al. | |
| 5,712,374 A | 1/1998 | Kuntsmann et al. | |
| 5,714,586 A | 2/1998 | Kunstmann et al. | |
| 5,739,350 A | 4/1998 | Kelly et al. | |
| 5,763,477 A | 6/1998 | Duvvuri et al. | |
| 5,773,001 A | 6/1998 | Hamann et al. | |
| 5,814,318 A | 9/1998 | Lonberg et al. | |
| 5,846,545 A | 12/1998 | Chari et al. | |
| 5,877,296 A | 3/1999 | Hamann et al. | |
| 5,892,063 A | 4/1999 | Zheng et al. | |
| 5,998,656 A | 12/1999 | Holton et al. | |
| 6,002,023 A | 12/1999 | Kingston et al. | |
| 6,005,079 A | 12/1999 | Casterman et al. | |
| 6,080,777 A | 6/2000 | Schiff | |
| 6,333,410 B1 | 12/2001 | Chari et al. | |
| 6,340,701 B1 | 1/2002 | Chari et al. | |
| 6,436,931 B1 | 8/2002 | Chari et al. | |
| 6,534,628 B1 | 3/2003 | Nilsson et al. | |
| 6,534,660 B1 | 3/2003 | Yongxin et al. | |
| 6,596,757 B1 | 7/2003 | Chari et al. | |

(Continued)

FOREIGN PATENT DOCUMENTS

| | | | |
|---|---|---|---|
| EP | 0239400 A2 | 9/1987 | |
| EP | 0519596 A1 | 12/1992 | |

(Continued)

OTHER PUBLICATIONS

Post, J Inter J Cancer, vol. 83, p. 571-6, 1999, IDS, XXX, filed on Jan. 31, 2005.*

(Continued)

Primary Examiner — Lei Yao
(74) Attorney, Agent, or Firm — Joyce von Natzmer; Agris & von Natzmer LLP

(57) ABSTRACT

Immunoconjugates comprising a targeting agent selectively targeting cell-surface expressed syndecan-1 and at least one effector molecule as well as in vitro and in vivo methods of using those immunocomjugates are disclosed. The effector molecule may have, in its native form, high non-selective cytotoxicity, but substantially no non-selective cytotoxicity when part of said immunoconjugate. Targeting agents include the antibody B-B4 as well as other agents that bind cell-surface expressed syndecan-1.

10 Claims, 9 Drawing Sheets

(56) References Cited

U.S. PATENT DOCUMENTS

| | | | |
|---|---|---|---|
| 6,706,708 | B2 | 3/2004 | Chari et al. |
| 6,716,821 | B2 | 4/2004 | Zhao et al. |
| 6,740,734 | B1 | 5/2004 | Nilsson et al. |
| 6,756,397 | B2 | 6/2004 | Zhao et al. |
| 2002/0006379 | A1 | 1/2002 | Hansen et al. |
| 2003/0004210 | A1 | 1/2003 | Chari et al. |
| 2003/0055226 | A1 | 3/2003 | Chari et al. |
| 2003/0109682 | A1 | 6/2003 | Santi et al. |
| 2004/0024049 | A1 | 2/2004 | Baloglu et al. |
| 2004/0082764 | A1 | 4/2004 | Kunz et al. |
| 2004/0087649 | A1 | 5/2004 | Chari et al. |
| 2004/0126379 | A1 | 7/2004 | Adolf et al. |
| 2004/0241817 | A1 | 12/2004 | Umana et al. |
| 2005/0123549 | A1* | 6/2005 | Payne et al. ............... 424/178.1 |
| 2005/0169933 | A1 | 8/2005 | Steeves et al. |
| 2009/0169570 | A1 | 7/2009 | Daelken et al. |
| 2009/0175863 | A1 | 7/2009 | Kraus et al. |
| 2009/0181038 | A1 | 7/2009 | Schulz et al. |
| 2009/0232810 | A1 | 9/2009 | Kraus et al. |

FOREIGN PATENT DOCUMENTS

| | | | |
|---|---|---|---|
| EP | 0592106 | A1 | 4/1994 |
| WO | WO 91/09967 | A1 | 7/1991 |
| WO | WO 91/10741 | A1 | 7/1991 |
| WO | WO 96/33735 | A1 | 10/1996 |
| WO | WO 96/34096 | A1 | 10/1996 |
| WO | WO 98/16654 | A1 | 4/1998 |
| WO | WO 98/24893 | A1 | 6/1998 |
| WO | WO 98/46645 | A2 | 10/1998 |
| WO | WO 98/50433 | A2 | 11/1998 |
| WO | 2010128087 | A2 | 11/2010 |

OTHER PUBLICATIONS

Vooijs et al, Cancer Immunol Immunother. vol. 42, p. 319-28, 1996.*
Tassone et al, Cancer Res, vol. 64, p. 4629-36, Jul. 2004.*
Tassone et al, Blood Nov. 16, 2003, vol. 102, 45th ASH meeting abstract 449s-450a (abstract).*
Tassone et al , Blood, vol. 104, p. 3688-96, published online, Aug. 3, 2004, IDS FFFFF.*
Chari et al, Cancer Res. 52: 127-131, 1992.*
Supiot et al, Cancer 94: 1202-9, 2002.*
US 5,831,021 (withdrawn).
Akkina RK, Rosenblatt JD, Campbell AG, Chen IS, Zack JA. Modeling human lymphoid precursor cell gene therapy in the SCID-hu mouse. Blood. 1994;84:1393-1398.
Anttonen A, Heikkila P, Kajanti M, Jalkanen M, Joensuu H. High syndecan-1 expression is associated with favourable outcome in squamous cell lung carcinoma treated with radical surgery. Lung Cancer. Jun. 2001; 32(3):297-305.
Barbareschi M, Maisonneuve P, Aldovini D, Cangi MG, Pecciarini L, Angelo Mauri F, Veronese 5, Caffo O, Lucenti A, Palma PD, Galligioni E, Doglioni C. High syndecan-1 expression in breast carcinoma is related to an aggressive phenotype and to poorer prognosis. Cancer. Aug. 1, 2003;98(3):474-83.
Bernfield M, Kokenyesi R, Kato M, Hinkes MT, Spring J, Gallo RL, Lose EJ. Biology of the syndecans: a family of transmembrane heparan sulfate proteoglycans. Annu Rev Cell Biol. 1992;8:365-393.
Beste G, Schmidt FS, Stibora T, Skerra A. Small antibody-like proteins with prescribed ligand specificities derived from the lipocalin fold. Proc. Natl. Acad. Sci. USA. 1999: 96, 1898-1903.
Bhattacharyya B, Wolff J. Maytansine binding to the vinblastine sites of tubulin. FEBS Lett. 1977;75:159-162.
Blättler WA and Chari RVJ. Drugs to Enhance the Therapeutic Potency of Anticancer Antibodies: Antibody-Drug Conjugates as Tumor-Activated Prodrugs. In: Ojima, I.; Vite, G.D. and Altmann, K.-H., Editors; 2001. Anticancer Agents—Frontiers in Cancer Chemotherapy, American Chemical Society, Washington, DC, pp. 317-338.

Bross PF, Beitz J, Chen G, Chen XH, Duffy E, Kieffer L, Roy S, Sridhara R, Rahman A, Williams G, Pazdur R. Approval summary: gemtuzumab ozogamicin in relapsed acute myeloid leukemia. Clin Cancer Res. 2001;7:1490-1496.
Carbone A, Gaidano G, Gloghini A, Ferlito A, Rinaldo A, Stein H. AIDS-related plasma-blastic lymphomas of the oral cavity and jaws: a diagnostic dilemma.Ann. Otol. Rhinol. Laryngol. 1999; 108: 95-99.
Carbone A et al. Reed-Sternberg cells of classical Hodgkin's disease react with the plasma cell-specific monoclonal antibody B-B4 and express human syndecan-1. Blood. 1997; 89:3787-94.
Carter P. Improving the efficacy of antibody-based cancer therapies. Nat Rev Cancer. 2001;1:118-129.
Chari RV, Martell BA, Gross JL, Cook SB, Shah SA, Blattler WA, McKenzie SJ, Goldmacher VS. Immunoconjugates containing novel maytansinoids: promising anticancer drugs. Cancer Res. 1992;52:127-131.
Chari RV, Jackel KA, Bourret LA, Derr SM, Tadayoni BM, Mattocks KM, Shah SA, Liu C, Blättler WA and Goldmacher VS. Enhancement of the selectivity and antitumor efficacy of a CC-1065 analogue through immunoconjugate formation. Cancer Res. 1995; 55: 4079-4084.
Charnaux N, Brule S, Chaigneau T, Saffar L, Sutton A, Hamon M. Prost C, Lievre N, Vita C, Gattegno L. RANTES (CCL5) induces a CCR5-dependent accelerated shedding of syndecan-1 (CD138) and syndecan-4 from HeLa cells and forms complexes with the shed ectodomains of these proteoglycans as well as with those of CD44. Glycobiology. 2005 5(2):119-130 (Sep. 8, 2004).
Chen BP, Galy A, Kyoizumi S, Namikawa R, Scarborough J, Webb S, Ford B, Cen DZ, Chen SC. Engraftment of human hematopoietic precursor cells with secondary transfer potential in SCID-hu mice. Blood. 1994;84:2497-2505.
Chilosi M, Adami F, Lestani M, Montagna L, Cimarosto L, Semenzato G, Pizzolo G, Menestrina F. CD138/syndecan-1: a useful immunohistochemical marker of normal and neoplastic plasma cells on routine trephine bone marrow biopsies. Mod Pathol. 1999;12:1101-1106.
Clement C, Vooijs, W.C., Klein, B., and Wijdenes, J. B-B2 and B-B4: two new mAb against secreting plasma cells. In: al. SFSe, ed. J. Leukocyte Typing V. Oxford: Oxford University Press; 1995:714-715.
Couturier O, Faivre-Chauvet A; Filippovich IV; Thedréz P, Saï-Maurel C; Bardiés M; Mishra AK; Gauvrit M; Blain G;Apostolidis C; Molinet R; Abbe JC; Bateille R; Wijdenes J; Chatal JF; Cherel M; Validation of 213Bi-alpha radioimmunotherapy for multiple myeloma. Clinical Cancer Research 5(10 Suppl.) (Oct. 1999) 3165s-3170s.
Davies EJ et al. , Blackhall FH, Shanks JH, David G, McGown AT, Swindell R, Slade RJ, Martin-Hirsch P, Gallagher JT, Jayson GC. Distribution and Clinical Significance of Heparan Sulfate Proteoglycans in Ovarian Cancer Clin Cancer Res. 2004; 10(15):5178-86.
Dhodapkar KM, Krasovsky J. Williamson B, Dhodapkar MV. Anti-tumor monoclonal abs enhance cross-presentation of Cellular antigens and the generation of myeloma-specific killer T cells by dendritic cells. J Exp Med. Jan. 7, 2002;195(1):125-33.
Dhodapkar MV, Krasovsky J, Olson K. T cells from the tumor microenvironment of patients with progressive myeloma can generate strong, tumor-specific cytolytic responses to autologous, tumor-loaded dendritic cells. Proc Natl Acad Sci U S A. Oct. 1, 2002;99(20):13009-13. Epub Sep. 16, 2002.
Dhodapkar MV, Abe E, Theus A, Lacy M. Langford JK, Barlogie B, Sanderson RD. Syndecan-1 is a multifunctional regulator of myeloma pathobiology: control of tumor cell survival, growth, and bone cell differentiation. Blood. 1998;91;2679-2688.
Dore JM, Morard F, Vita N, Wijdenes J. Identification and location on syndecan-1 core protein of the epitopes of B-B2 and B-B4 monoclonal antibodies. FEBS Lett. 1998:426:67-70.
Dowell JA, Korth-Bradley J, Liu H, King SP, Berger MS. Pharmacokinetics of gemtuzumab ozogamicin, an antibody-targeted chemotherapy agent for the treatment of patients with acute myeloid leukemia in first relapse. J Clin Pharmacol. 2001;41:1206-1214.

(56) References Cited

OTHER PUBLICATIONS

Edinger M, Sweeney TJ, Tucker AA, Olomu AB; Negrin RS, Contag CH. Noninvasive assessment of tumor cell proliferation in animal models. Neoplasia. 1999;1;303-310.

Gattei V. Godeas C, Degan M, Rossi FM, Aldinucci D, Pinto A. Characterization of Anti-CD138 monoclonal antibodies as tools for investigating the molecular polymorphism of syndecan-1 in human lymphoma cells. Br J Haematol. 1999;104:152-162.

Hamann PR, Hinman LM, Beyer CF, Lindh D, Upeslacis J, Flowers DA, Bernstein I. An anti-CD33 antibody-calicheamicin conjugate for treatment of acute myeloid leukemia. Choice of linker. Bioconjug Chem. 2002;13:40-46.

Han I, Park H, Oh ES. New insights into syndecan-2 expression and tumourigenic activity in colon carcinoma cells. J Mol Histol. 2004: 35(3):319-26.

Horvathova M, Gaillard, J.-P., Liutard, J., Duperray, C., Lavabre-Bertrand, T., Bourquard, P et al. In: al. SFSe, ed. Leucocyte Typing V. Oxford: Oxford University Press; 1995:713-714.

Jokimaa V, Inki P, Kujari H, Hirvonen O, Ekholm E, Anttila L.. Expression of syndecan-1 in human placenta and decidua.. Placenta. Mar.-Apr. 1998;19(2-3):157-63.

Jokimaa VI, Kujari HP, Ekholm EM, Inki PL, Anttila L. Placental expression of syndecan 1 is diminished in preeclampsia. Am J Obstet Gynecol, Dec. 2000;183(6):1495-8.

Krebs B, Rauchenberger R, Reiffert S, Rothe C, Tesar M, Thomassen E, Cao M, Dreier T, Fischer D, Hoss A et al. High-throughput generation and engineering of recombinant human antibodies. 2001. J. Immunol. Methods 254, pp. 67-84.

Kupchan SM, Sneden AT, Branfman AR, Howie GA, Rebhun LI, McIvor WE, Wang RW, Schnaitman TC. Structural requirements for antileukemic activity among the naturally occurring and semisynthetic maytansinoids. J Med Chem. 1978;21:31-37.

Kyoizumi S, Baum CM, Kaneshima H, McCune JM, Yee EJ, Namikawa R. Implantation and maintenance of functional human bone marrow in SCID-hu mice. Blood. 1992;79:1704-1711.

Kyoizumi S, Murray LJ, Namikawa R. Preclinical analysis of cytokine therapy in the SCID-hu mouse. Blood. 1993;81;1479-1488.

Liu C, Tadayoni BM, Bourret LA, Mattocks KM, Derr SM, Widdison WC, Kedersha NL, Ariniello PD, Goldmacher VS, Lambert JM. Blattler WA, Chari RV. Eradication of large colon tumor xenografts by targeted delivery of maytansinoids. Proc Natl Acad Sci U S A. 1996;93:8618-8623.

McCune JM, Namikawa R, Kaneshima H, Shultz LD, Lieberman M, Weissman IL. The SCID-hu mouse: murine model for the analysis of human hematolymphoid differentiation and function. Science, 1988;241:1632-1639.

Mennerich D, Vogel A, Klaman I, Dahl E, Lichtner RB, Rosenthal A, Pohlenz HD, Thierauch KH, Sommer A, Shift of syndecan-1 expression from epithelial to stromal cells during progression of solid tumours. Eur J Cancer. Jun. 2004; 40(9):1373-82.

Mosmann T. Rapid colorimetric assay for cellular growth and survival: application to proliferation and cytotoxicity assays. J Immunol Methods. 1983;65:55-63.

Mukunyadzi P, Sanderson RD, Fan CY, Smoller BR. The level of syndecan-1 expression is a distinguishing feature in behavior between keratoacanthoma and invasive cutaneous squamous cell carcinoma. Mod Pathol. Jan. 2002;15(1):45-9.

Namikawa R. Ueda R, Kyoizumi S. Growth of human myeloid leukemias in the human marrow environment of SCID-hu mice. Blood. Oct. 15, 1993;82 (8 :2526-36.

O'Connell FP, Pinkus JL, Pinkus GS. CD138 (Syndecan-1), a Plasma Cell Marker Immunohistochemical Profile in Hematopoietic and Nonhematopoietic Neoplasms. Am J Clin Pathol 2004; 121;254-263.

Ojima. I, Geng X, Wu X, Qu C, Borella CP, Xie H, Wilhelm SD, Leece BA, Bartle LM, Goldmacher VS and Chari RV. Tumor-specific novel taxoid-monoclonal antibody conjugates. 2002. J. Med. Chem. 45, pp. 5620-5623.

Olafsen,T, Cheung, CC, Yazaki, PJ, Li L, Sundaresan G, Gambhir SS, Sherman, MA, Williams, LE, Shively, JE, Raubitschek. AA, and Wu, AM. Covalent disulfide-linked anti-CEA diabody allows site-specific conjugation and radiolabeling for tumor targeting applications. 2004; Prot. Eng. Design & Selection 17:1:21-27.

Orosz Z, Kopper L. Syndecan-1 expression in different soft tissue tumours. Anticancer Res. 2001: 21(1B):733-7.

Padlan, EA. A possible procedure for reducing the immunogenicity of antibody variable domains while preserving their ligand-binding properties. Mol. Immunol. 1991; 28: 489-498.

Palacios M, Perez MA, Scolnik MD. B-B4 monoclonal antibody and identification of human bone marrow plasma cells (including response) Br J Haematol. 1997;96:654-657.

Payne G. Progress in immunoconjugate cancer therapeutics. Cancer Cell. 2003;3:207-212.

Pegram MD, Lipton A, Hayes DF, Weber BL, Baselga JM, Tripathy D, Baly D, Baughman SA, Twaddell T, Glaspy JA and Slamon DJ. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. 1998. J. Clin. Oncol. 16, pp. 2659-2671.

Post J, Vooijs WC, Bast BJ, De Gast GC. Efficacy of an anti-CD138 immunotoxin and doxorubicin on drug-resistant and drug-sensitive myeloma cells. Int J Cancer. Nov. 12, 1999;83(4):571-6.

Rawstron AC, Owen RG, Davies FE, Johnson RJ, Jones RA, Richards SJ, Evans PA, Child JA, Smith GM, Jack AS, Morgan GJ. Circulating plasma cells in multiple myeloma: characterization and correlation with disease stage. Br J Haematol. 1997;97:46-55.

Remillard S, Rebhun LI, Howie GA, Kupchan SM. Antimitotic activity of the potent tumor inhibitor maytansine. Science. 1975;189:1002-1005.

Rintala M, Inki P, Klemi P, Jalkanen M, Grenman S. Association of syndecan-1 with tumor grade and histology in primary invasive cervical carcinoma. Gynecol Oncol. Dec. 1999;75(3):372-8.

Roguska MA, Pedersen JT, Keddy CA, Henry AH, Searle SJ, Lambert JM, Goldmacher VS, Blattler WA, Rees AR, Guild BC. Humanization of murine monoclonal antibodies through variable domain resurfacing. Proc Natl Acad U S A. 1994;91:969-973.

Ross JS, Gray K, Gray G, Worland PJ, Rolfe M. Anticancer Antibodies, Am J Clin Path. (Apr. 17, 2003).

Ross S, Spencer SD, Holcomb I , Tan C. Hongo J, Devaux B, Rangell L, Keller GA, Schow P. Steeves RM, Lutz RJ, Frantz G, Hillan K, Peale F, Tobin P, Eberhard D, Rubin MA, Lasky LA, Koeppen H. Prostate stem cell antigen as therapy target: tissue expression and in vivo efficacy of an immunoconjugate. Cancer Res, May 1, 2002:62(9):2546-53.

Sanderson RD, Lalor P, Bernfield M. B lymphocytes express and lose syndecan at specific stages of differentiation. Cell Regul. 1989;1:27-35.

Sandhu JS, Clark BR, Boynton EL, Atkins H, Messner H, Keating A, Hozumi N. Human hematopoiesis in SCID mice implanted with human adult cancellous bone. Blood. 1996;88:1973-1982.

Sasaki A, Boyce BF, Story B, Wright KR, Chapman M, Boyce R, Mundy GR, Yoneda T. Bisphosphonate risedronate reduces metastatic human breast cancer burden in bone in nude mice. Cancer Res. 1995;55:3551-3557.

Schneider U, van Lessen A, Huhn D, Serke S. Two subsets of peripheral blood plasma cells defined by differential expression of CD45 antigen. Br J Haematol, 1997;97:56-64.

Sebestyen A, Berczi L, Mihalik R, Paku S, Matolcsy A, Kopper L. Syndecan-1 (CD138) expression in human non-Hodgkin lymphomas. Br J Haematol. 1999; 104(2):412-9.

Seftalioglu A, Karakus S. Syndecan-1/CD138 expression in normal myeloid, acute lymphoblastic and myeloblastic leukemia cells. Acta Histochem. 2003;105:213-221.

Seftalioglu A, Karakus S, Dundar S, Can B, Erdemli E, Irmak MK, Oztas E, Korkmaz C, Yazar F, Cavusoglu I. Syndecan-1 (CD138) expression in acute myeloblastic leukemia cells—an immuno electron microscopic study. Acta Oncol. 2003:42:71-74.

Senter PD, Doronina S, Cerveny C, Chace D, Francisco J, Klussman K, Mendelsohn B, Meyer D, Siegall CB, Thompson J et al. Cures and regressions of established tumours with monoclonal antibody auristatin conjugates. Abstract #2062, Proc. Am. Assoc. Can. Res. (San Francisco, CA: American for Cancer Res.) 2002; 43 March: 414-15.

(56) References Cited

OTHER PUBLICATIONS

Sievers EL, Larson R.A., Stadtmauer, E.A., Estey, E., Lowenberg, B., Dombret, H., Karanes, C., Theobald, M., Bennett, J.M., Sherman, M.L. et al. Efficacy and safety of gemtuzumab ozogamicin in patients with CD33-positive acute myeloid leukemia in first relapse. 2001. J. Clin. Oncol. 19, pp. 3244-3254.

Sievers EL and Linenberger M. Mylotarg: antibody-targeted chemotherapy comes of age. 2001. Curr. Opin. Oncol. 13, pp. 522-527.

Smith R., Single chain antibody variable region fragments; www.stanford.edu/~smithr/science/scfv.html (last updated on May 2001).

Stanley MJ, Stanley MW, Sanderson RD, Zera R. Syndecan-1 expression is induced in the stroma of infiltrating breast carcinoma. Am J Clin Pathol. Sep. 1999;112(3):377-83.

Studnicka GM, Soares S, Better M, Williams RE, Nadell R, Horwitz AH. Human-engineered monoclonal antibodies retain full specific binding activity by preserving non-CDR complementarity-modulating residues.Protein Eng. 1994: 7(6): 805-814.

Sun RX, Lu ZY, Wijdenes J, Brochier J, Hertog C, Rossi JF, Klein B. Large scale and clinical grade purification of syndecan-1+ malignant plasma cells. J Immunol Methods. Jun. 23, 1997;205(1):73-9.

Tolcher AW, Ochoa L, Hammond LA, Patnaik A, Edwards T, Takimoto C, Smith L, de Bono J, Schwartz G, Mays T, Jonak ZL, Johnson R, DeWitle M, Martino H, Audette C, Maes K, Chari RV, Lambert JM, Rowinsky EK. Cantuzumab mertansine, a maytansinoid immunoconjugate directed to the CanAg antigen: a phase I, pharmacokinetic, and biologic correlative study. J Clin Oncol. 2003;21:211-222.

Urashima M, Chen BP, Chen S, Pinkus GS, Bronson RT, Dedera DA, Hoshi Y, Teoh G, Ogata A, Treon SP, Chauhan D, Anderson KC. The development of a model for the homing of multiple myeloma cells to human bone marrow. Blood. 1997;90:754-765.

Vogel CW. Preparation of immunoconjugates using antibody oligosaccharide moieties. Methods in Molecular Biology: Bioconjugation protocols strategies and methods. 2004:283:087-108.

Vooijs WC, Post J, Wijdenes J, Schuurman HJ, Bolognesi A, Polito L, Stirpe F, Bast EJ, de Gast GC. Efficacy and toxicity of plasma-cell-reactive monoclonal antibodies B-B2 and B-B4 and their immunotoxins. Cancer Immunol Immunother. 1996;42:319-328.

Ward, E.S., D. Gussow, A.D. Griffiths, P.T. Jones, and G. Winter. Binding activities of a repertoire of single immunoglobin variable domains secreted from *Escherichia coli*. Nature. 1989.341:544-546.

Wargalla UC, Reisfeld RA. Rate of internalization of an immunotoxin correlates with cytotoxic activity against human tumor cells. Proc. Natl. Acad. Sci. USA. 1989;86:5146-5150.

Wijdenes J, Vooijs WC. Clement C, Post J, Morard F, Vita N, Laurent P, Sun RX, Klein B, Dore JM. A plasmocyte selective monoclonal antibody (B-B4) recognizes syndecan-1. Br J Haematol. 1996;94:318-323.

Wijdenes J, Dore JM, Clement C, Vermot-Desroches C. CD138, J Biol Regul Homeost Agents. Apr.-Jun. 2002;16(2):152-5.

Wiksten JP, Lundin J, Nordling S, Lundin M, Kokkola A, von Boguslawski K, Haglund C. Epithelial and stromal syndecan-1 expression as predictor of outcome in patients with gastric cancer. Int J Cancer. Jan. 20, 2001;95(1):1-6.

Witzig TE, Kimlinger TK, Ahmann GJ, Katzmann JA, Greipp PR. Detection of myeloma cells in the peripheral blood by flow cytometry. Cytometry. 1996;26:113-120.

Xie H, Audette C, Hoffee M, Lambert JM, Blättler W. Pharmacokinetics and biodistribution of the antitumor immunoconjugate, cantuzumab mertansine (huC242-DM1), and its two components in mice.J Pharmacol Exp Ther, Mar. 2004;308(3):1073-82.

Yang M, Jiang P, An Z, Baranov E, Li L, Hasegawa S, Al-Tuwaijri M, Chishima T, Shimada H, Moossa AR, Hoffman RM. Genetically fluorescent melanoma bone and organ metastasis models. Clin Cancer Res. 1999;5:3549-3559.

Yang M, Baranov E, Jiang P, Sun FX, Li XM, Li L, Hasegawa S, Bouvet M, Al-Tuwaijri M, Chishima T, Shimada H, Moossa AR, Penman S, Hoffman RM. Whole-body optical imaging of green fluorescent protein-expressing tumors and metastases. Proc Natl Acad Sci U S A. 2000;97:1206-1211.

Tassone et al., "Cytotoxic activity of the maytansinoid immunoconjugate B-B4-DM1 against CD138+ multiple myeloma cells," Blood First Edition Paper, prepublished online Aug. 3, 2004; DOI 10.1182/blood-2004-03-0963.

Cavallaro et al.; "α2-macroglobulin receptor mediates binding and cytotoxicity of plant ribosome-inactivating proteins;" in Eur. J. Biochem.; vol. 232; 1995; pp. 165-171.

Casellas et al., Chapter 19, "Immunotoxin Enhancers," in Cancer Treatment and Research, William L. McGuire, series editor, Kluwer Academic Publishers, Boston/Dordrecht/Lancaster, vol. 37, 1988, pp. 351-369.

Thrush et al., "Immunotoxins: An Update," in Ann. Rev. Immunol., vol. 14, 1996, pp. 49-71.

Shih et al., "Internalization and Intracellular Processing of an Anti-B-Cell Lymphoma Monoclonal Antibody, LL2," in Int. J. Cancer, vol. 56, 1994, pp. 538-545.

Austin et al., "Oxidizing Potential of Endosomes and Lysosomes Limits Intracellular Cleavage of Disulfide-Based Antibody-Drug Conjugates," in PNAS, vol. 102(50), Dec. 13, 2005, pp. 17987-17992.

Chari, "Targeted Delivery of Chemotherapeutics: Tumor-Activated Prodrug Therapy," in Advanced Drug Delivery Reviews, vol. 31, 1998, pp. 89-104.

Goldmacher et al., "Cytotoxicity of Gelonin and Its Conjugates With Antibodies Is Deteremined by the Extent of Their Endocytosis," in Journal of Cellular Physiology, vol. 141, 1989, pp. 222-234.

Supiot et al., "Compariosn of the Biologic Effects of MA5 and B-B4 Monoclonal Antibody Labeled with Iodine-131 and Bismuth-213 on Multiple Myeloma," Cancer, vol. 94, No. S4, pp. 1202-1209, 2002.

\* cited by examiner

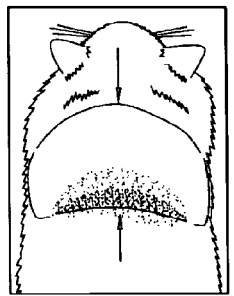
FIG.6A
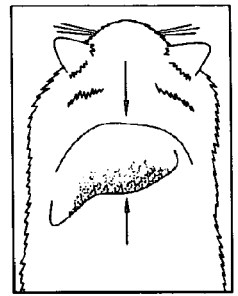
FIG.6B
FIG.6C
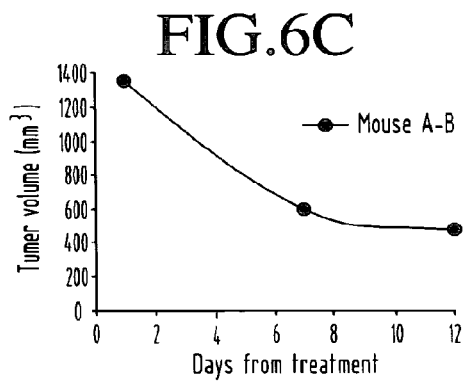
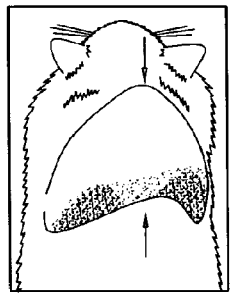
FIG.6D
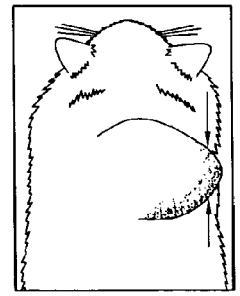
FIG.6E
FIG.6F
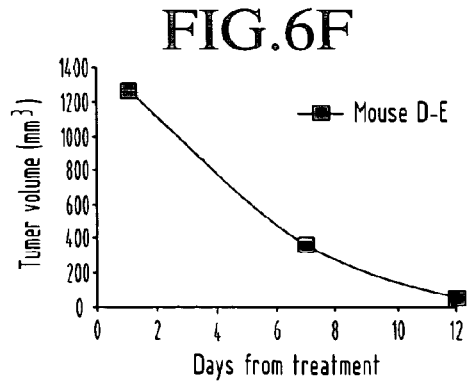

IMMUNOCONJUGATES TARGETING SYNDECAN-1 EXPRESSING CELLS AND USE THEREOF

This application is a divisional of U.S. application Ser. No. 10/975,434, filed Oct. 29, 2004, the content of which is incorporated herein by reference, which claims the benefit of U.S. provisional Application No. 60/605,394, filed Aug. 30, 2004, the content of which is incorporated herein by reference.

BACKGROUND

This invention pertains to immunoconjugates and their use in different indications. In particular, the present invention relates to immunoconjugates, the delivery of their effector molecule(s) to target sites and the site specific release of the effector molecule(s) in, at or near target cells, tissues and organs. More particularly, the present invention relates to immunoconjugates comprising one or more syndecan-1 targeting agent and highly potent effector molecules, which are attached to the targeting agent. The effector molecule is activated by cleavage/dissociation from the targeting agent portion of the immunoconjugate in, at or near the target cells, tissues or organs.

The publications and other materials, including patents, used herein to illustrate the invention and, in particular, to provide additional details respecting the practice are incorporated by reference. For convenience, the publications are referenced in the following text by author and date and are listed alphabetically by author in the appended bibliography.

A substantial body of research has concentrated on the development of systems in which an effector agent can be selectively delivered to a desired location or cell population, i.e., a system for a more targeted treatment of ailments with fewer toxic side effects. In spite of considerable progress that has been achieved, many of those delivery systems for the treatment of various diseases, for example, the treatment of cancer, are still often ineffective or subject the patient to considerable risk.

Immunoconjugates comprise at least one targeting agent attached to at least one effector molecule. Such immunoconjugates can be categorized according to their effector molecules into, for example, drug immunoconjugates, immunotoxin conjugate and radioimmunoconjugates (Payne, 2003).

Efficiency in killing cells is one key factor in the usefulness of an immunoconjugate. Efficiency can be influenced by the potency of the effector molecule (Blättler and Chari, 2001), by the ability of the effector to retain its potency (Chari et al., 1995; Liu et al., 1996; Ojima et al., 2002; Senter et al., 2002 and Sievers and Linenberger, 2001), By the tumor accessibility (Charter, 2001), by the level of expression of the target antigen on the target cell, targeting agent affinity, and by the ability of the target cell to internalize the immunoconjugate (Wargalla, 1989). In the initial development period of immunoconjugates, the efficiencies of conjugates having a drug as an effector molecule often were disappointing compared to the free drug.

In response, immunoconjugates with highly cytotoxic effector toxin molecules were constructed. However, while the efficiencies of this new generation of immunoconjugates were much improved, they were often immunogenic in humans, inducing neutralizing antibodies both to the toxin protein and to the mouse monoclonal antibody. In response, "humanized" antibodies conjugated to nonimmunogenic effector molecules were developed (Payne, 2003).

In the context of both highly cytotoxic drugs and toxins conjugated to a targeting agent, systemic toxicity has to be considered. If the cytotoxic drug or the toxin is highly cytotoxic, the immunoconjugate has to reach its target site without adversely affecting the host on its way. Accordingly, if the immunoconjugate circulates, for example, in the bloodstream to reach its target site, then this should occur without a substantial release of active drug. Thus, ideally, a highly cytotoxic drug or toxin of an immunoconjugate is only activated upon reaching its target.

Specificity is another factor critical for the usability of an immunoconjugate. The immunoconjugate has to be able to selectively interact with the target cells. Particularly for in vivo applications, it is critical that the immunoconjugate does not have substantial adverse effects on essential non-target cells. Thus, both the cellular target of the immunoconjugate and the targeting agent of the immunoconjugate have to be carefully selected to ensure specificity (Blättler and Chari, 2001).

It has also been considered important that immunoconjugates comprising targeting antibodies demonstrate pharmacokinetic and tissue distribution characteristics similar to those of corresponding antibodies (Xie, 2003).

First successes have been achieved with immunoconjugates. For example, MYLOTARG, a conjugate of an anti-CD33 humanized monoclonal antibody and the highly cytotoxic DNA-damaging agent calicheamicin, has been recently approved by the FDA as the first drug immunoconjugate for clinical treatment of certain indications of myeloid leukemia (Bross, 2001; Hamann, 2002; Dowell, 2001).

However, there remains a need to develop effective immunoconjugates for a wide array of indications.

SUMMARY OF THE INVENTION

The present invention pertains in one embodiment to an immunoconjugate comprising
  at least one targeting agent selectively targeting cell-surface expressed syndecan-1,
  at least one effector molecule,
  wherein the effector molecule has, in its native form, high non-selective cytotoxicity,
  wherein the targeting agent is functionally attached to said effector molecule to form the immunoconjugate, and
  wherein the effector molecule has substantially no non-selective cytotoxicity when part of said immunoconjugate.

The cytotoxicity of the effector molecule, in its native form, on cells targeted by said targeting antibody may be higher or about the same as the cytotoxicity of the immunoconjugate on said targeted cells. The effector molecule may have, in its native form, a potency of about $10^{-14}$-$10^{-7}$, preferably a potency of about $10^{-13}$-$10^{-7}$M, of about $10^{-12}$-$10^{-7}$M, of about $10^{-12}$-$10^{-8}$M, most preferably of about $10^{-11}$-$10^{-8}$ M, which includes any narrower potency ranges encompassed by the ranges specified above, such as, but not limited to, a potency of about $10^{-11}$-$10^{-10}$ M. The effector molecule may be a maytansinoid, in particular DM1, DM3 or DM4, a CC1065 analogue, a calicheamicin or a taxane. In certain embodiments, the effector molecule may have a molecular weight of less than 5 kDa, in particular less than 2 kDa, more in particular less than 1 kDa and in between about 600 and about 800 Da.

The targeting agent may be a targeting antibody, which includes fragments of antibodies, or non-immunoglobulin targeting molecule.

The targeting antibody may be derived from an antibody that internalizes poorly. In certain embodiments, the targeting antibody may be derived from the antibody B-B4.

The present invention is also directed to a pharmaceutical composition comprising an effective amount of the immunoconjugate described above and one or more pharmaceutically acceptable excipients.

The present invention is also directed to a kit comprising, in separate containers, pharmaceutical compositions for use in combination to inhibit, delay and/or prevent the growth of tumors and/or spread of tumor cells, wherein one container comprises an effective amount of above described pharmaceutical composition, and wherein, a separate container comprises a second pharmaceutical composition comprising an effective amount of an agent for the inhibition, delay and/or prevention of the growth of tumors and/or spread of tumor cells, and one or more pharmaceutically acceptable excipients. The agent in said second pharmaceutical composition may be a chemotherapeutic agent or another immunoconjugate.

In one embodiment, the invention is directed to a method for treating, inhibiting, delaying and/or preventing the growth of tumor cells in a cell culture containing syndecan-1 expressing tumor cells and non-tumor cells, comprising administering an effective amount of the above described immunoconjugate. The effective amount induces, in certain embodiments, cell death or continuous cell cycle arrest of said syndecan-1 expressing tumor cells. The cells in said cell culture may be obtained from a cancer patient and may, after administration of said effective amount of said immunoconjugate, be reimplanted into said cancer patient. The cells in said cell culture may be isolated from a patient suffering from an hematologic malignancy and/or a solid tumor comprising syndecan-1 expressing cells, in particular from a patient suffering from one of the following: multiple myeloma, ovarian carcinoma, kidney carcinoma, gall bladder carcinoma, breast carcinoma, prostate cancer, lung cancer, colon carcinoma, Hodgkin's and non-Hodgkin's lymphoma, chronic lymphocytic leukemia (CLL), acute lymphoblastic leukemia (ALL), acute myeloblastic leukemia (AML), a solid tissue sarcoma or a colon carcinoma.

The present invention is also directed to a method of inhibiting, delaying and/or preventing the growth of a tumor comprising syndecan-1 expressing tumor cells and/or spread of syndecan-1 expressing tumor cells in a patient in need thereof, comprising
administering to the patient at least one immunoconjugate in a growth of the tumor and/or spreading of the tumor cells inhibiting or reducing amount,
wherein the immunoconjugate selectively inhibits, delays or prevents the growth and/or spread of syndecan-1 expressing cells. The patient may, in this embodiment of the invention, suffer from an hematologic malignancy and/or a solid tumor comprising syndecan-1 expressing cells, in particular from one of the following: multiple myeloma, ovarian carcinoma, kidney carcinoma, gall bladder carcinoma, breast carcinoma, prostate cancer, lung cancer, colon carcinoma, Hodgkin's and non-Hodgkin's lymphoma, chronic lymphocytic leukemia (CLL), acute lymphoblastic leukemia (ALL), acute myeloblastic leukemia (AML), a solid tissue sarcoma or a colon carcinoma. An effector molecule of the immunoconjugate may, in this embodiment, exhibit, in its native form, high non-selective cytotoxicity.

The invention is also directed to a method for inhibiting, delaying and/or preventing the growth of a tumor and/or spread of malignant tumor cells in a patient in need thereof, comprising
(a) administering to the patient one or more cancer drugs and/or radiation in an amount effective to reduce tumor load; and
(b) administering to the patient at least one immunoconjugate in a growth of a tumor and/or spreading of tumor cells inhibiting, delaying or preventing amount,
wherein the immunoconjugate selectively inhibits, delays or prevents the growth and/or spread of syndecan-1 expressing cells; (a) and (b) may hereby be performed consecutively in two consecutive treatment regimes. The drug of (a) and the immunoconjugate of (b) may also be administered in a single administration step.

The present invention is also directed to a method for treating a subject having a condition that would benefit from the selective suppression of myeloma cell survival, the method comprising:
(a) providing at least one immunoconjugate that selectively binds to syndecan-1 expressed on myeloma cells; and
(b) administering the immunoconjugate to the subject to selectively decrease survival or growth of said myeloma cells of the subject. The immunoconjugate may comprise a B-B4 targeting antibody. The immunoconjugate may, in this embodiment, comprise a maytansinoid effector molecule. The selective suppression of myeloma cell survival may also induce growth arrest or apoptosis in myeloma cells.

BRIEF DESCRIPTION OF THE DRAWINGS

FIGS. 6A to F show the activity of B-B4-DM1 on large tumor xenografts of human CD138$^+$ OPM multiple myeloma.

DETAILED DESCRIPTION OF VARIOUS AND PREFERRED EMBODIMENTS

Figure 1A:
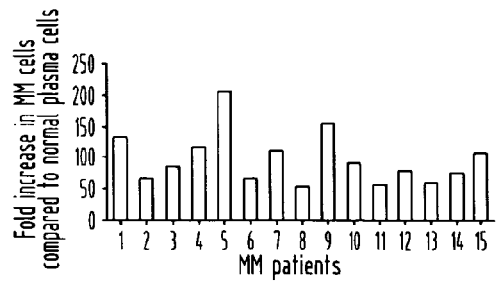
FIGS. 1A-1F show the expression of CD138 in multiple myeloma (MM) cells.

The present invention relates to immunoconjugates and the delivery of their effector molecule(s) to target sites and the site specific release of effector(s) molecule in, at or near target cells, tissues and organs. More particularly, the present invention relates to immunoconjugates comprising syndecan-1 targeting agents and potent effector molecules. The effector molecules are covalently linked, chelated or otherwise associated with the targeting agent. The effector molecules may be activated by cleavage/dissociation from the targeting agent portion of the immunoconjugate at the target site.

The immunoconjugates according to the present invention are administered to a subject in need of therapeutic treatment or to cells isolated from such a subject in need of therapeutic treatment. The effector molecule or molecules may be released from the immunoconjugate by cleavage/dissociation in, at or close to the target cell, tissue or organ.

As one example, the immunoconjugate comprises the antibody B-B4 and at least one highly cytotoxic drug or toxin as an effector molecule and is administered to a patient with cancer. In this example, a therapeutically effective amount of the immunoconjugate is administered intravenously to a patient so that it concentrates in the cancer cells. The effector molecule or molecules are released from the antibody target by natural means.

As a second example, the immunoconjugate comprises the antibody B-B4 and at least one highly cytotoxic drug and is administered to a cell population isolated from a patient with cancer. In this example, a cell death or continuous cell cycle arrest inducing amount of the immunoconjugate is administered to the cell population so that it concentrates in the cancerous cells. The effector molecule or molecules are released from the targeting antibody by natural means or external means to induce cell death or continuous cell cycle arrest in the cancer cells.

As a third example, the immunoconjugate comprises the antibody B-B4 and at least one highly cytotoxic drug or an immunotoxin as an effector molecule and is administered to a patient with cancer. In this example, a therapeutically effective amount of the immunoconjugate is administered intravenously to a patient so that it concentrates in the cancerous cells. The effector molecule or molecules are released from the antibody target by an external means to induce cell death or continuous cell cycle arrest in the cancer cells.

Targeting Agent:

A targeting agent according to the present invention is able to associate with a molecule expressed by a target cell and includes peptides and non-peptides. In particular, targeting agents according to the present invention include targeting antibodies and non-immunoglobulin targeting molecules, which may be based on non-immunoglobulin proteins, including, but not limited to, AFFILIN® molecules, ANTI-CALINS® and AFFIBODIES®. Non-immunoglobulin targeting molecules also include non-peptidic targeting molecules including targeting DNA and RNA oligonucleotides (aptamers).

Targeting Antibody:

A targeting antibody according to the present invention is or is based on a natural antibody or is produced synthetically or by genetic engineering and binds to an antigen on a cell or cells (target cell(s)) of interest. A targeting antibody according to the present invention includes a monoclonal antibody, a polyclonal antibody, a multispecific antibody (for example, a bispecific antibody), or an antibody fragment. The targeting antibody may be engineered to, for example, improve its affinity to the target cells (Ross, 2003) or diminish its immunogenicity. The targeting antibody may be attached to a liposomal formulation including effector molecules (Carter, 2003). An antibody fragment comprises a portion of an intact antibody, preferably the antigen binding or variable region of the intact antibody. Examples of antibody fragments according to the present invention include Fab, Fab', F(ab')$_2$, and Fv fragments, but also diabodies; domain antibodies (dAb) (Ward, 1989; U.S. Pat. No. 6,005,079); linear antibodies; single-chain antibody molecules; and multispecific antibodies formed from antibody fragments. In a single chain variable fragment antibody (scFv) the heavy and light chains (VH and VL) can be linked by a short amino acid linker having, for example, the sequence (glycine$_4$serine)$_n$, which has sufficient flexibility to allow the two domains to assemble a functional antigen binding pocket. Addition of various signal sequences may allow for more precise targeting of the targeting antibody. Addition of the light chain constant region (CL) may allow dimerization via disulphide bonds, giving increased stability and avidity. Variable regions for constructing the scFv can, if a mAb against a target of interest is available, be obtained by RT-PCR which clones out the variable regions from mRNA extracted from the parent hybridoma. Alternatively, the scFv can be generated de novo by phage display technology (Smith, 2001). A bispecific antibody according to the present invention may, for example, have at least one arm that is reactive against a target tissue and one arm that is reactive against a linker moiety (United States Patent Publication 20020006379). A bispecific antibody according to the present invention may also bind to more than one antigen on a target cell (Carter, 2003). An antibody according to the present invention may be modified by, for example, introducing cystein residues to introduce thiol groups (Olafsen, 2004).

In accordance with the present invention, the targeting antibody may be derived from any source and may be, but is not limited to, a camel antibody, a murine antibody, a chimeric human/mouse antibody or a chimeric human/monkey antibody, in particular, a chimeric human/monkey antibody with the monkey portion stemming from a cynomolgus monkey. Humanized antibodies are antibodies that contain sequences derived from a human-antibody and from a non-human antibody and are also within the scope of the present invention. Suitable methods for humanizing antibodies include CDR-grafting (complementarity determining region grafting) (EP 0 239 400; WO 91/09967; U.S. Pat. Nos. 5,530,101; and 5,585,089), veneering or resurfacing (EP 0 592 106; EP 0 519 596; Padlan, 199; Studnicka et al., 1994; Roguska et al., 1994), chain shuffling (U.S. Pat. No. 5,565,332) and DEIMMUNOSATION™ method (Biovation, LTD). In CDR-grafting, the mouse complementarity-determining regions (CDRs) from, for example, mAb B-B4 are grafted into human variable frameworks, which are then joined to human constant regions, to create a human B-B4 antibody. Several antibodies humanized by CDR-grafting are now in clinical use, including MYLOTARG (Sievers et al., 2001) and HECEPTIN (Pegram et al, 1998).

The resurfacing technology uses a combination of molecular modeling, statistical analysis and mutagenesis to alter the non-CDR surfaces of antibody variable regions to resemble the surfaces of known antibodies of the target host. Strategies and methods for the resurfacing of antibodies, and other methods for reducing immunogenicity of antibodies within a different host, are disclosed, for example, in U.S. Pat. No. 5,639,641. Human antibodies can be made by a variety of methods known in the art including phage display methods. See also U.S. Pat. Nos. 4,444,887, 4,716,111, 5,545,806, and 5,814,318; and international patent application publications WO 98/46645, WO 98/50433, WO 98/24893, WO 98/16654, WO 96/34096, WO 96/33735, and WO 91/10741.

Fully human antibodies may also been used. Those antibodies can be selected by the phage display approach, where CD138 or an antigenic determinant thereof is used to selectively bind phage expressing, for example, B-B4 variable regions (see, Krebs, 2001). This approach is advantageously coupled with an affinity maturation technique to improve the affinity of the antibody.

In one embodiment, the targeting antibody is, in its unconjugated form, moderately or poorly internalizable. Moderate internalization constitutes about 30% to about 75% internalization of antibody, poor internalization constitutes about 0.01% to up to about 30% internalization after 3 hours incubation at 37° C. In another preferred embodiment the targeting antibody binds to CD138, for example, antibodies B-B4, BC/B-B4, B-B2, DL-101, 1 D4, MI15, 1.BB.210, 2Q1484, 5F7, 104-9, 281-2 in particular B-B4. Preferably the targeting antibody binds primarily to cell-surface expressed CD138. In another embodiment, the targeting antibody does not substantially bind non-cell-surface expressed CD138. When, in the context of the present invention, the name of a specific antibody is combined with the term "targeting antibody" such as "B-B4 targeting antibody," this means that this targeting antibody has the binding specificity of the antibody B-B4. If a targeting antibody is said to be "derived from" a specified antibody, this means that this targeting antibody has the binding specificity of this antibody, but might take any form consistent with the above description of a targeting antibody. If, in the context of the present invention, for example, a targeting antibody is said to do something "selectively" such as "selectively targeting cell-surface expressed syndcan-1" or, to be "selective" for something, this means that there is a significant selectivity (i.e. a higher affinity towards CD138-positive cells compared with CD138-negative cells) for, in case of the example provided, cell-surface expressed syndecan-1, compared to any other antigens and adverse side effects in a given environment are substantially avoided due to this selectivity.

Non-Immunoglobulin Targeting Molecules:

Non-immunoglobulin targeting molecules according to the present invention include targeting molecules derived from non-immunoglobulin proteins as well as non-peptidic targeting molecules. Small non-immunoglobulin proteins which are included in this definition are designed to have specific affinities towards, in particular surface expressed CD138. These small non-immunoglobulin proteins include scaffold based engineered molecules such as AFFILIN molecules that have a relatively low molecular weight such as between 10 kDa and 20 kDa. Appropriate scaffolds include, for example, gamma crystalline. Those molecules have, in their natural state, no specific binding activity towards the target molecules. By engineering the protein surfaces through locally defined randomization of solvent exposed amino acids, completely new binding sites are created. Former non-binding proteins are thereby transformed into specific binding proteins. Such molecules can be specifically designed to bind a target, such as CD138, and allow for specific delivery of one or more effector molecules (see, SCIL proteins GmbH, 2004). Another kind of non-immunoglobulin targeting molecules are derived from lipocalins, and include, for example ANTICALINS®, which resemble in structure somewhat immunoglobulins. However, lipocalins are composed of a single polypeptide chain with 160 to 180 amino acid residues. The binding pocket of lipocalins can be reshaped to recognize a molecule of interest with high affinity and specificity (see, for example, Beste et al., 1999). Artificial bacterial receptors such as those marketed under the trademark AFFIBODY artificial bacterial receptors (AFFIBODY AB) are also within the scope of the present invention. These artificial bacterial receptor molecules are small, simple proteins and may be composed of a three-helix bundle based on the scaffold of one of the IgG-binding domains of Protein A (*Staylococcus aureus*). These molecules have binding properties similar to many immunoglobulins, but are substantially smaller, having a molecular weight often not exceeding 10 kDa and are also comparatively stable. Suitable artificial bacterial receptor molecules are, for example, described in U.S. Pat. Nos. 5,831,012; 6,534,628 and 6,740,734. Non-peptidic targeting molecules include, but are limited to, to DNA and RNA oligonucleotides that bind to CD138 (aptamers).

Effector Molecule:

An effector molecule according to the present invention is a molecule or a derivative, or an analogue thereof that is attached to a targeting agent and exerts a desired effect, for example apoptosis, or another type of cell death, or a continuous cell cycle arrest on the target cell or cells. Effector molecules according to the present invention include molecules that can exert desired effects in a target cell and include, but are not limited to, toxins, drugs, in particular low molecular weight cytotoxic drugs, radionuclides, biological response modifiers, pore-forming agents, cytotoxic enzymes, prodrug activating enzymes, antisense oligonucleotides, antibodies or cytokines as well as functional derivatives or analogues/fragments thereof.

In a preferred embodiment, the effector increases internal effector delivery of the immunoconjugate, in particular when the natural form of the antibody on which the targeting antibody of the immunoconjugate is based is poorly internalizable. In another preferred embodiment the effector is, in its native form, non-selective. In certain embodiments the effector has high non-selective toxicity, including systemic toxicity, when in its native form. The "native form" of an effector molecule of the present invention is an effector molecule before being attached to the targeting agent to form an immunoconjugate. In another preferred embodiment, the non-selective toxicity of the effector molecule is substantially eliminated upon conjugation to the targeting agent. In another preferred embodiment, the effector molecule causes, upon reaching the target cell, death or continuous cell cycle arrest in the target cell. A drug-effector molecule according to the present invention includes, but is not limited to, a drug including, for example, small highly cytotoxic drugs that act as inhibitors of tubulin polymerization such as maytansinoids, dolastatins, auristatin and crytophycin; DNA alkylating agents like CC-1065 analogues or derivatives (U.S. Pat. Nos. 5,475,092; 5,585,499; 6,716,821) and duocarmycin; enediyne antibiotics such as calicheamicin and esperamicin; and potent taxoid (taxane) drugs (Payne, 2003). Maytansinoids and calicheamicins are particularly preferred. An effector maytansinoid includes maytansinoids of any origin, including, but not limited to synthetic maytansinol and maytansinol analogue and derivative. Doxorubicin, daunomycin, methotrexate, vinblastine, neocarzinostatin, macromycin, trenimon and α-amanitin are some other effector molecules within the scope of the present invention. Also within the scope of the present invention are antisense DNA molecules as effector molecules. When the name of, for example, a specific drug or class of drugs is combined herein with the term "effector" or "effector molecule," reference is made to an effector of an immunoconjugate according to the present invention that is based on the specified drug or class of drugs.

Maytansine is a natural product originally derived from the Ethiopian shrub *Maytenus serrata* (Remillard, 1975; U.S. Pat. No. 3,896,111). This drug inhibits tubulin polymerization, resulting in mitotic block and cell death (Remillard, 1975; Bhattacharyya, 1977; Kupchan, 1978). The cytotoxicity of maytansine is 200-1000-fold higher than that of anti-cancer drugs in clinical use that affect tubulin polymerization, such as Vinca alkaloids or taxol. However, clinical trials of maytansine indicated that it lacked a therapeutic window due to its high systemic toxicity. Maytansine and maytansinoids are highly cytotoxic but their clinical use in cancer therapy has been greatly limited by their severe systemic side-effects primarily attributed to their poor selectivity for tumors. Clinical trials with maytansine showed serious adverse effects on the central nervous system and gastrointestinal system.

Maytansinoids have also been isolated from other plants including seed tissue of *Trewia nudiflora* (U.S. Pat. No. 4,418,064)

Certain microbes also produce maytansinoids, such as maytansinol and C-3 maytansinol esters (U.S. Pat. No. 4,151,042).

The present invention is directed to maytansinoids of any origin, including synthetic maytansinol and maytansinol analogues which are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,371,533; 4,424,219 and 4,151,042.

In a preferred embodiment, the maytansinoid is a thiol-containing maytansinoid and is more preferably produced according to the processes disclosed in U.S. Pat. No. 6,333, 410 to Chari et al or in Chari et al. (Chari, 1992).

DM-1 ($N^2$-deacetyl-$N^2$-(3-mercapto-1-oxopropyl)-maytansine) is a preferred effector molecule in the context of the present invention. DM1 is 3- to 10-fold more cytotoxic than maytansine, and has been converted into a pro-drug by linking it via disulfide bond(s) to a monoclonal antibody directed towards a tumor-associated antigen. Certain of these conjugates (sometimes called "tumor activated prodrugs" (TAPs)) are not cytotoxic in the blood compartment, since they are activated upon associating with a target cells and internalized, thereby releasing the drug (Blättler, 2001). Several antibody-DM1 conjugates have been developed (Payne, 2003), and been evaluated in clinical trials. For example, huC242-DM1 treatment in colorectal cancer patients was well tolerated, did not induce any detectable immune response, and had a long circulation time (Tolcher, 2003).

Other particularly preferred maytansinoids comprise a side chain that contains a sterically hindered thiol bond such as, but not limited to, maytansinoids $N^{2'}$-deacetyl-$N^{2'}$-(4-mercapto-1-oxopentyl)-maytansine, also referred to as "DM3," and $N^{2'}$-deacetyl-$N^{2'}$-(4-methyl-4-mercapto-1-oxopentyl)-maytansine, also referred to as "DM4."

DNA alkylating agents are also particularly preferred as effector molecules and include, but are not limited to, CC-1065 analogues or derivatives. CC-1065 is a potent anti-tumor-antibiotic isolated from cultures of *Streptomyces zelensis* and has been shown to be exceptionally cytotoxic in vitro (U.S. Pat. No. 4,169,888). Within the scope of the present invention are, for examples the CC-1065 analogues or derivatives described in U.S. Pat. Nos. 5,475,092, 5,585,499 and 5,739,350. As the person skilled in the art will readily appreciate, modified CC-1065 analogues or derivatives as described in U.S. Pat. No. 5,846,545 and prodrugs of CC-1065 analogues or derivatives as described, for example, in U.S. Pat. No. 6,756,397 are also within the scope of the present invention. In certain embodiments of the invention, CC-1065 analogues or derivatives may, for example, be synthesized as described in U.S. Pat. No. 6,534,660.

Another group of compounds that make preferred effector molecules are taxanes, especially highly potent ones and those that contain thiol or disulfide groups. Taxanes are mitotic spindle poisons that inhibit the depolymerization of tubulin, resulting in an increase in the rate of microtubule assembly and cell death. Taxanes that are within the scope of the present invention are, for example, disclosed in U.S. Pat. Nos. 6,436,931; 6,340,701; 6,706,708 and United States Patent Publications 20040087649; 20040024049 and 20030004210. Other taxanes are disclosed, for example, in U.S. Pat. No. 6,002,023, U.S. Pat. No. 5,998,656, U.S. Pat. No. 5,892,063, U.S. Pat. No. 5,763,477, U.S. Pat. No. 5,705, 508, U.S. Pat. No. 5,703,247 and U.S. Pat. No. 5,367,086. As the person skilled in the art will appreciate, PEGylated taxanes such as the ones described in U.S. Pat. No. 6,596,757 are also within the scope of the present invention.

Calicheamicin effector molecules according to the present invention include gamma 1I, N-acetyl calicheamicin and other derivatives of calicheamicin. Calicheamicin binds in a sequence-specific manner to the minor groove of DNA, undergoes rearrangement and exposes free radicals, leading to breakage of double-stranded DNA, resulting in cell apoptosis and death. One example of a calicheamicin effector molecule that can be used in the context of the present invention is described in U.S. Pat. No. 5,053,394.

Immunoconjugate:

An immunoconjugate according to the present invention comprises at least one targeting agent, in particular targeting antibody, and one effector molecule. The immunoconjugate might comprise further molecules for example for stabilization. For immunoconjugates, the term "conjugate" is generally used to define the operative association of the targeting agent with one or more effector molecules and is not intended to refer solely to any type of operative association, and is particularly not limited to chemical "conjugation". So long as the targeting agent is able to bind to the target site and the attached effector functions sufficiently as intended, particularly when delivered to the target site, any mode of attachment will be suitable. The conjugation methods according to the present invention include, but are not limited to, direct attachment of the effector molecule to the targeting antibody, with or without prior modification of the effector molecule and/or the targeting antibody or attachment via linkers. Linkers can be categorized functionally into, for example, acid labile, photosensitive, enzyme cleavable linkers etc. Other suitable linkers may include disulfide bonds and non-cleavable bonds, such as, but not limited to Sulfosuccinimidyl maleimidom-ethyl cyclohexane carboxylate (SMCC), which is a heterobi-functional linker capable of linking compounds with SH-containing compounds. Bifunctional and heterobifunctional linker molecules, such as carbohydrate-directed heterobi-functional linker molecules, such as S-(2-thiopyridyl)-L-cys-teine hydrazide (TPCH), are also within the scope of the present invention (Vogel, 2004). The effector molecule, such as a maytansinoid, may be conjugated to the targeting antibody via a two reaction step process, including as a first step modification of the targeting antibody with a cross-linking reagent such as N-succinimidyl pyridyldithiopropionate (SPDP) to introduce dithiopyridyl groups into the targeting antibody. In a second step, a reactive maytansinoid having a thiol group, such as DM1, may be added to the modified antibody, resulting in the displacement of the thiopyridyl groups in the modified antibody, and the production of disul-fide-linked cytotoxic maytansinoid/antibody conjugate (U.S. Pat. No. 5,208,020). However, one-step conjugation processes such as the one disclosed in United States Patent Publication 20030055226 to Chari et al are also within the scope of the present invention. In one embodiment of the present invention multiple effector molecules of the same or different kind are attached to a targeting antibody.

CC-1065 analogues or derivatives may be conjugated to the targeting agent via for example PEG linking groups as described in U.S. Pat. No. 6,716,821.

Calicheamicins may be conjugated to the targeting antibodies via linkers (U.S. Pat. No. 5,877,296 and U.S. Pat. No. 5,773,001) or according to the conjugation methods disclosed in U.S. Pat. No. 5,712,374 and U.S. Pat. No. 5,714,586. Another preferred method for preparing calicheamicin conjugates is disclosed in Unites States Patent Publication 20040082764.

The immunoconjugates of the present invention also include recombinant fusion proteins.

The present invention takes advantage of the property of antibodies, in particular monoclonal antibodies, to bind to specific antigen targets, in particular, the property of certain antibodies to bind to CD138.

CD138 or sydecan-1 (also described as SYND1; SYNDECAN; SDC; SCD1; CD138 ANTIGEN, SwissProt accession number: P18827 human) is a membrane glycoprotein that was originally described to be present on cells of epithelial origin, and subsequently found on hematopoietic cells (Sanderson, 1989). In malignant hematopoiesis, CD138 is highly expressed on the majority of MM cells, ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), solid tissue sarcomas, colon carcinomas as well as other hematologic malignancies and solid tumors that express syndecan-1 (Carbone et al., 1999; Sebestyen et al., 1999; Han et al., 2004; Charnaux et al., 2004; O'Connell et al., 2004; Orosz and Kopper, 2001).

Other cancers that have been shown to be positive for CD138 expression are many ovarian adenocarcinomas, transitional cell bladder carcinomas, kidney clear cell carcinomas, squamous cell lung carcinomas; breast carcinomas and uterine cancers (see, for example, Davies et al., 2004; Barbareschi et al., 2003; Mennerich et al., 2004; Anttonen et al., 2001; Wijdenes, 2002).

In the normal human hematopoietic compartment, CD138 expression is restricted to plasma cells (Wijdenes, 1996; Chilosi, 1999) and is not expressed on peripheral blood lymphocytes, monocytes, granulocytes, and red blood cells. In particular, CD34+ stem and progenitor cells do not express CD138 and anti-CD138 mAbs do not affect the number of colony forming units in hematopoietic stem cell cultures (Wijdenes, 1996). In non-hematopoietic compartments, CD138 is mainly expressed on simple and stratified epithelia within the lung, liver, skin, kidney and gut. Only a weak staining was seen on endothelial cells (Bernfield, 1992; Vooijs, 1996). It has been reported that CD138 exists in polymorphic forms in human lymphoma cells (Gattei, 1999).

Monoclonal antibodies antibodies B-B4, BC/B-B4, B-B2, DL-101, 1 D4, MI15, 1.BB.210, 2Q1484, 5F7, 104-9, 281-2 in particular B-B4 have been reported to be specific to CD138. Of those B-B4, 1 D4 and MI15 recognized both the intact molecule and the core protein of CD138 and were shown to recognize either the same or closely related epitopes (Gattei, 1999). B-B4 has the advantage of not recognizing soluble CD138, but only CD138 in membrane bound form (Wijdenes, 2002).

B-B4, a murine IgG1 mAb, binds to a linear epitope between residues 90-95 of the core protein on human syndecan-1 (CD138) (Wijdenes, 1996; Dore, 1998). Consistent with the expression pattern of CD138, B-B4 was shown to strongly react with plasma cell line RPMI8226, but not to react with endothelial cells. Also consistent with the expression pattern of CD138, B-B4 also reacted with epithelial cells lines A431 (keratinocyte derived) and HepG2 (hepatocyte derived). An immunotoxin B-B4-saporin was also highly toxic towards the plasma cell line RPM18226, in fact considerably more toxic than free saporin. However, from the two epithelial cell lines tested, B-B4-saporin showed only toxicity towards cell line A431, although in a clonogenic assay B-B4 saporin showed no inhibitory effect on the outgrowth of A431 cells (Vooijs, 1996). Other researchers reported lack of specificity of MM-associated antigens against tumors (Couturier, 1999).

The reactivity of B-B4 with tissue of various organs is shown in Table 1, the reactivity of B-B4 with cell lines of different origins is shown in Table 2. The reactivity was determined by immunohistochemistry (Table 1) and cytofluorography (Table 2). The number of (+) signs indicate the intensity of the reaction.

TABLE 1

Reactivity of B-B4 with tissues of various organs (immunohistochemistry)

| Organ | Tissue | B-B4 |
|---|---|---|
| Blood | Normal plasma cells | +++ |
| Blood | MM patient cells | +++ |
| Kidney | Tubular epithelium | − |
| Kidney | Glomerular | − |
| Kidney | Urothelium | ++ |
| Kidney | Smooth muscle of hilus | − |
| Liver | Sinusoid endothelium | − |
| Liver | Biliary epithelium | − |
| Liver | Hepatocytes | ++ |
| Lung | Alveolar epithelium | ++ |
| Lung | Bronchial epithelium | + |
| Lung | Blood vessel | − |
| Lung | Bronchial gland | ++ |
| Duodenum | Crypts epithelium | ++ |
| Duodenum | Glands | ++ |
| Duodenum | Chorion lymphocytes | ++ |
| Duodenum | Smooth muscle | − |
| Duodenum | Blood vessels | − |
| Heart | Myocytes | ++ (cytoplasmic) |
| Spleen | Red pulp | + |
| Various organs | Muscle | − |
| Various organs | Connective tissue | − |
| Various organs | Nervous tissue | − |
| Various organs | Epithelium | +++ |
| Various organs | Endothelium | + |
| Cell lines | MM cell lines | +++ |

TABLE 2

Reactivity of B-B4 with cell lines of different origins (Cytofluorography)

| Cell line | Cell type | B-B4 |
|---|---|---|
| RPMI 8226 | Multiple myeloma | +++ |
| U266 | Multiple myeloma | +++ |
| UM-1 | Multiple myeloma | +++ |
| XG-1 | Multiple myeloma | +++ |
| Daudi | EBV-infected LCL | − |
| Ramos | EBV-infected LCL | − |
| Jijoye | EBV-infected LCL | − |
| BJAB | Burkitt lymphoma | − |
| Raji | Burkitt lymphoma | − |
| BTL-1 | LCL | − |
| BTL-6 | LCL | − |
| KM-3 | Pre-B | + |
| REH | Pre-B | − |
| NALM-6 | Pre-B | + |
| ROS | Pre-B | − |
| 697 | Pre-B | − |
| CEM | T-cell | − |
| Jurkat | T-cell | − |
| HL-60 | Myeloid | − |
| U937 | Myeloid | + |
| HEL | Myeloid | − |
| KG1A | Myeloid | − |
| K562 | Erythroid | ++ |
| A341 | Epithelial | +++ |
| HepG | Hepatocytic | ++ |
| HUVEC | Endothelial | + |
| Peripheral blood | Monocyte | − |
| Peripheral blood | B-cell (CD19+) | − |

TABLE 2-continued

Reactivity of B-B4 with cell lines of different origins (Cytofluorography)

| Cell line | Cell type | B-B4 |
|---|---|---|
| Peripheral blood | T-cell (CD3+) | − |
| Peripheral blood | Granulocytes | − |
| Bone marrow | (CD34+, CD33+, CD19+, CD20+, CD10+, CD3+, CD19+, CD14+, CD38+) cells | − |
| Bone marrow | Plasma cells | ++ |
| Bone marrow | Myeloma cells/CD38 high | +++ |
| Tonsil | (CD19+, CD38+) cells | − |
| Patient sample ALL | B-cell | − |
| Patient sample CLL | B-cell | − |
| Patient sample Hodgkin | Reed-Sternberg cell | ++ |

The activity of immunoconjugates on a cellular level has been described, for example, for huC242-DM1 (Immunogen, Inc.), an immunoconjugate comprising the antibody huC242 and the maytansinoid DM1, an inhibitor of tubulin polymerization described above. The activity of this immunoconjugate at the cellular level was described to include the following steps: (1) binding of the immunoconjugate to the antigen expressed on a cancer cell, (2) the internalization of the conjugate-antigen complex by the cancer cell, and (3) release of DM1, thereby allowing DM1 to reach its intracellular target tubulin and to inhibit tubulin polymerization (Xie, 2003). This multi-step attachment, internalization and release model forms the rationale behind the development of tumor activated prodrugs (TAPs) (Immunogen, 2003). Similar uptake mechanisms have been described for immunoconjugates based on anti-PSCA antibodies, which were reported to be internalized via caveolae (Ross, 2002).

The present invention is useful in the treatment of, but is not limited to, cancers, in particular, multiple myeloma, ovarian carcinoma, kidney carcinoma, gall bladder carcinoma, breast carcinoma, prostate cancer, lung cancer, colon carcinoma, Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), solid tissue sarcomas, colon carcinomas as well as other hematologic malignancies and solid tumors that express syndecan-1 (Carbone et al., 1999; Sebestyen et al., 1999; Han et al., 2004; Charnaux et al., 2004; O'Connell et al., 2004; Orosz and Kopper, 2001).

The immunoconjugates according to the present invention can be administered by any route, including intravenously, parenterally, orally, intramuscularly, intrathecally or as an aerosol. The mode of delivery will depend on the desired effect. A skilled artisan will readily know the best route of administration for a particular treatment in accordance with the present invention. The appropriate dosage will depend on the route of administration and the treatment indicated, and can readily be determined by a skilled artisan in view of current treatment protocols.

Pharmaceutical compositions containing an immunoconjugate of the present invention as the active ingredient can be prepared according to conventional pharmaceutical compounding techniques. See, for example, Remington's Pharmaceutical Sciences, 17th Ed. (1985, Mack Publishing Co., Easton, Pa.). Typically, an antagonistic amount of active ingredient will be admixed with a pharmaceutically acceptable carrier. The carrier may take a wide variety of forms depending on the form of preparation desired for administration, for example, intravenous, oral, parenteral, intrathecal, transdermal, or by aerosol.

For oral administration, the immunoconjugate can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the immunoconjugate may be dissolved in a pharmaceutical carrier and administered as either a solution or a suspension. Illustrative of suitable carriers are water, saline, phosphate buffer solution (PBS), dextrose solutions, fructose solutions, ethanol, or oils of animal, vegetative or synthetic origin. The carrier may also contain other ingredients, for example, preservatives, suspending agents, solubilizing agents, buffers and the like. When the immunoconjugate are being administered intracerebroventricularly or intrathecally, they may also be dissolved in cerebrospinal fluid.

In accordance with the present invention, MM is treated as follows, with use of the B-B4-DM1 conjugate as an example. This example is not intended to limit the present invention in any manner, and a skilled artisan could readily determine other immunoconjugates of the present invention and other treatment regimes which could be utilized for the treatment of diseases such as MM. Due to the selective expression of CD138 on patient MM cells on via the blood stream accessible cells, the specificity of B-B4 and the stability of the B-B4-DM1 conjugate in the bloodstream, the immunoconjugate removes the systemic toxicity of DM1 and provides an opportunity to target the delivery of the DM1-effector molecule(s). The immunoconjugates of this invention provide a means for the effective administration of the effector molecules to cell sites where the effector molecules can be released from the immunoconjugates. This targeted delivery and release provides a significant advance in the treatment of multiple myeloma, for which current chemotherapy methods sometimes provide incomplete remission.

In accordance with the present invention, in particular solid tumors may also be treated as follows with use of B-B4-DM1, as an example. This example is not intended to limit the present invention in any manner, and a skilled artisan could readily determine other immunoconjugates of the present invention and other treatment regimes which could be utilized for the treatment of solid tumors. The tumor is first treated to reduce the size of the tumor, for example chemotherapeutically or radioactively. Subsequent administration of the immunoconjugates of this invention provides a means for eliminating residual cancer cells. The administration of the immunoconjugate allows specific targeting of these residual cells and release of the effector molecules at the target site. This targeted delivery and release provides a significant advance in the treatment of residual cancer cells of solid tumors, for which current chemotherapy methods sometimes provide incomplete remission.

The present invention is further described by reference to the following Examples, which are offered by way of illustration and are not intended to limit the invention in any manner. Standard techniques well known in the art or the techniques specifically described below were utilized.

Materials and Methods
Preparation of mAb-DM1 Conjugate

The thiol-containing maytansinoid DM1 was synthesized from the microbial fermentation product ansamitocin P-3, as previously described by Chari (Chari et al, 1992). Characterization of murine B-B4 (Wijdenes, 1996) and preparation of humanized C242 (huC242) (Roguska, 1994) have been previously described. Antibody-drug conjugates were prepared as described by Liu et al (Liu, 1996). An average of 3.5 DM1 molecules was linked per antibody molecule.

Cell Lines and Patient Cells

CD138$^+$ dexamethasone (Dex)-sensitive MM.1S and Dex-resistant MM.1R, Ocy-My5, OPM1 and OPM2 human MM cell lines and CD138$^-$ Waldenstrom Macroglobulinemia (WM) WSU-WM and the lymphoma (LB) SUDHL4 cell lines were used. Cell lines were cultured in RPMI-1640 medium (GIBCO) supplemented with 10% fetal bovine serum (FBS; Hyclone, Logan, Utah), L-glutamine, penicillin, and streptomycin (GIBCO) (denoted below as RPMI complete medium). Plasma cells (PC) and bone marrow (BM) cells were isolated using Ficoll-Hypaque density gradient sedimentation from BM aspirates, obtained from MM patients following informed consent. BM cells were separated. BMSCs were obtained by long-term cultures of BM cells (4-8 weeks) in RPMI 1640 medium supplemented with 20% FBS.

Gene Expression Analysis and Data Analysis: Expression of Cd138 in MM Patients

Expression of CD138 on normal plasma cells and patient MM cells was evalutated. BM aspirate samples from normal donors and patients with MM were treated with 0.86% ammonium chloride to lyse red blood cells. PC were then isolated by positive immunomagnetic bead selection using anti-CD138 antibodies and Magnet Assisted Cell Sorting ("MACS," Miltenyi Biotech). Purity of plasma cells (>95%) was assessed by flow cytometric (Becton-Dickinson "FAC-Sort") monitoring for CD38$^+$/CD45$^{lo}$ phenotype as well as forward and side scatter and morphological characteristics. Total RNA was isolated from 5×10$^6$ cells utilizing an "RNeasy® kit" (Qiagen Inc., Valencia, Calif.). Total RNA (10-15 µg) was reverse-transcribed to get cDNA using the "Superscript® II RT kit" (Invitrogen Life Technologies, Carlsbad, Calif.). cDNA was used in an in vitro transcription reaction to synthesize biotin-labeled cRNA utilizing "ENZO® RNA labeling kit" (Enzo Diagnostics, Inc., Farmingdale, N.Y.). Labeled cRNA was purified with the "RNeasy® Mini-kit" (Qiagen Inc., Valencia, Calif.) and quantitated. Purified cRNA (15 µg) was hybridized to Human Genome U133 (HG-U133) GeneChip® arrays (Affymetrix, Inc.) representing approximately 33,000 human genes, and GeneChip® arrays were scanned on a GeneArray® Scanner (Affymetrix, Inc., Santa Clara, Calif.). Normalization of arrays and calculation of expression values was performed using the DNA-Chip Analyzer ("dChip") program. Arrays were normalized based on relative signal produced for an invariant subset of genes. This model-based method was used for probe selection and computing expression values. By pooling hybridization information across multiple arrays, it was possible to assess standard errors for the expression level indexes. This approach also allowed automatic probe selection in the analysis stage to reduce errors due to cross-hybridizing probes and image contamination.

Antibody Internalization

Internalization of B-B4 antibody was examined with a cultured CD138$^+$ cell line by flow cytometry and under a fluorescent microscope. The antibody was modified by Alexa 488 dye (Molecular Probes), and the fluorescence of the non-internalized antibody bound to cells was quenched by exposure to an "anti-Alexa antibody" (Molecular Probes). Thus, semi-quantitatively discrimination between surface-bound and internalized antibody was possible. B-B4 was poorly internalized.

Colorimetric Survival Assay

Survival of CD138$^+$ and CD138$^-$ cells upon administration of B-B4-DM1, B-B4 and DM1 was examined using a tetrazolium colorimetric assay (CellTiter 96® Non-Radioactive Cell Proliferation Assay; Promega, Wis.), as previously described (Mossmann, 1983). Cells (1×10$^4$) were plated in 24-well plates in 1 ml RPMI complete medium and then treated as indicated. At the end of each treatment, cells were incubated with 150 µl of Dye Solution and then incubated for 4 h at 37° C. A solubilization/stop solution was then added to each well under vigorous pipetting to dissolve the formazan crystals. Absorbance was measured at 570 nm, and cell viability was estimated as percentage of untreated controls. All experiments were repeated 3 times, and each experimental condition was repeated in triplicate wells in each experiment. Data reported are average values±SD of 3 representative experiments.

Cell Proliferation Assay

The effect of B-B4-DM1 on cell proliferation was measured by the extent of [$^3$H]-thymidine (NEN Life Science Products, Boston, Mass.) incorporation. Cells (2×10$^4$ cells/well) were incubated in 96-well culture plates in the presence of 70%-80% confluent BMSCs at 37° C. with or without a test-agent (in triplicate wells). [$^3$H]-thymidine (0.5 µCi) was then added to each well for the last 8 h. Cells were harvested onto glass filters with an automatic cell harvester (Cambridge Technology, Cambridge, Mass.) and counted using a Micro-Beta® Trilux counter (Wallac, Gaithersburgh, Md.).

Detection of Apoptosis

Dual staining with FITC-labeled Annexin V and propidium iodide (PI) was carried out to detect induction of apoptotic cell death by B-B4-DM1. After treatment of 1×10$^6$ tumor cells for 48 h, cells were washed with PBS and re-suspended in 100 □l of HEPES buffer containing Annexin V-FITC and propidium iodide (PI) (Annexin V-FLUOS staining kit; Roche Diagnostic, Indianapolis, Ind.). Following 15 min incubation at room temperature, cells were analyzed using a Coulter Epics XL flow cytometer for the presence of an Annexin V-FITC-positive/PI-negative apoptotic cell population.

Cell Cycle Analysis

1×10$^6$ MM cells were incubated with or without a test-agent for 48 h, washed with PBS, permeabilized by a 30 min exposure to 70% ethanol at 4° C., incubated with PI (50-µg/mL) in 0.5 ml PBS containing 20 U/mL Rnase A (Roche) for 30 min at room temperature, and analyzed for DNA content by cell-associated fluorescence using a flow cytometer and CellQuest™ software.

In Vivo Activity
Human MM Xenograft Murine Model

In this model, CB-17 SCID mice were subcutaneously (s.c.) inoculated in the interscapular area with 5×10$^6$ OPM1 or OPM2 cells in 100 µl of RPMI-1640 medium. Treatment was initiated after the detection of palpable tumors. Tumor growth was measured weekly in two dimensions using a caliper, and volume was expressed in mm$^3$ using the formula: V=0.5a×b$^2$, where a and b are the long and short diameter of the tumor, respectively. Tumor size was evaluated from the first day of treatment until day of first sacrifice. The survival time is defined as the time interval between start of the experiment and either death or day of sacrifice. Mice were treated intavenously (i.v.) with vehicle alone (PBS), unconjugated B-B4 (13.3 µg/ml), B-B4-DM1 (conjugate containing 75 or 150 µg DM1/Kg per day), or control huC242-DM1 (150 µg DM1/Kg per day), for a total of 3 days. In addition, two mice bearing very large tumors (average size of 1309±60 mm$^3$) were treated with B-B4-DM1 (150 µg DM1/kg per day) for a total of 3 days and observed for changes in the tumor size.

Autofluorescent GFP$^+$ Human MM Xenograft Model

Procedures for stably transfection of green fluorescent protein (GFP) in tumor cells and use have been previously described (Yang, 1999; Yang 2000). Five mice were injected s.c. with GFP$^+$ OPM1 cells as described above. Mice were monitored by whole-body fluorescence imaging using "Illumatool Bright Light System LT-9900" (Lightools Research, Encinitas, Calif.). After accurate cutaneous shave of tumor area, fluorescence imaging results were digitally captured by a Sony® DSC-P5™ digital camera (Sony, New York, N.Y.) and analyzed with Adobe PhotoShop® 4.0.

SCID-hu Mouse Model

Human fetal bones were obtained from products of conceptions of second trimester abortions in compliance with state and federal regulations (Advanced Bioscience Resourses, ABR; Alameda, Calif.). The implantation of human fetal long bone grafts into SCID mice to produce SCID-hu mice has been previously described (McCune et al, 1988; Namikawa et al, 1988; Kyoizumi et al, 1993; Akkina et al, 1994; Chen et al, 1994; Sandhu et al, 1996; Urashima, 1997). In brief, the femurs or tibias of 19 to 23 gestational week fetuses were cut into fragments and implanted s.c. into SCID mice. After approximately 8 weeks, 2 to 5×10$^6$ BM cells from a MM patient or Ocy-My5 MM cells were injected in 50 µl PBS directly into human bone of SCID-hu hosts. Production and level of human paraprotein in mouse serum was an indicator of myeloma engrafinent and growth. At least 2 consecutive measurements, of increasing levels of circulating human immunoglobulin (huIg), signified human MM cell growth.

Measurement of Serum Paraprotein Concentration

Blood (50-100 µl) was withdrawn from the tail vein for measurement of human paraprotein in murine serum using ELISA (Bethyl, Montgomery, Tex.). Goat anti-human λ and κ antisera were used for capture and goat anti-human λ or κ HRP conjugates were used for detection.

Histopatological Analysis

Excised bone grafts were fixed in 10% buffered formalin; skeletal tissues were decalcified with 14% EDTA and embedded in paraffin by previously described standard techniques (Sasaki, 1995). Sections were then stained with H & E (Hematoxylin and eosin) for histopathological examination. Immunoperoxidase studies were performed on paraffin sections using an indirect technique as described (Urashima, 1997). Rabbit anti-human λ and κ antisera were used for detection of MM cells in fetal bone.

Statistical Analysis

Statistical significance of differences was determined using Student's t-test. Differences were considered significant when p<0.05.

Results and Discussion

Figure 1B:
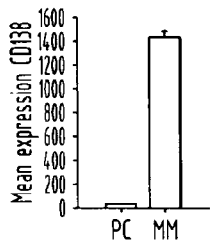
Figure 1C:
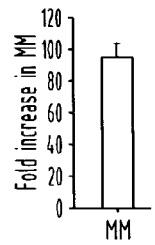

CD138 is expressed on patient MM cells and is the most important target Ag for identification and selection of these cells. However previous reports show heterogenous CD138 expression on MM cells (Wijdenes, 1996; Dhodapkar, 1998; Witzig, 1996; Schneider, 1997; Rawstron, 1997). The expression of CD138 on patient MM cells was measured by gene profiling and flow cytometry. FIGS. 1A to 1C show the CD138 gene expression profiles of normal plasma cells (n=3) and patient MM cells (n=15) measured utilizing HG-U133 GeneChip® array (Affymetrix) data. FIG. 1A shows the individual fold increase in intensity of CD138 gene expression compared to normal PC; FIG. 1B shows the mean of intensity of CD138 gene expression in normal PC (n=3) and patient MM cells (n=15) and FIG. 1C the mean fold increase intensity of CD138 gene expression in MM cells (n=15) compared to normal PC (n=3). As can be seen, CD138 was expressed in all 15 MM specimens (100%) examined at a 95±8-fold mean increase in intensity relative to normal plasma cells.

Figure 1D:
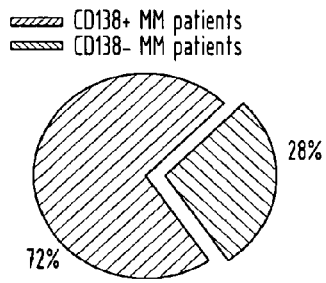
Figure 1E:
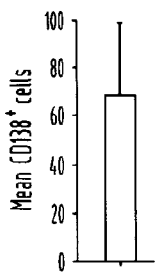
Figure 1F:
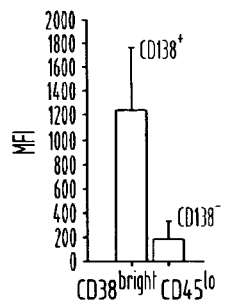

Furthermore, flow cytometry was used to assess cell surface expression of CD138 on MM cells from 25 patients. Expression of CD138 on the CD38$^{bright}$CD45$^{lo}$ cell population was assessed both by percentage of positive cells, and by mean fluorescence intensity (MFI). FIG. 1D shows the percentage of patients expressing CD138$^+$ MM cells, as determined by flow cytometry on fresh BM aspirate samples. FIG. 1E shows the percentage of CD138$^+$ MM cells in CD138$^+$ patients on fresh BM aspirates and FIG. 1F shows MFI of CD138$^+$ or CD138$^-$ MM cells within CD38$^{bright}$CD45$^{lo}$ population. As can be seen from FIG. 1D 18 of 25 patients (72%) expressed CD138, with a mean of 68±31% CD138$^+$ cells (FIG. 1E) and MFI of 1234±539 (range: 166-2208) (FIG. 1F). Taken together, these results indicate that CD138 is highly expressed in patient MM cells.

These results were consistent with previous reports showing CD138 expression on 60% and 100% of cases (Horvathova, 1995; Wijdenes, 1996). Possible explanations for the variability in CD138 detection by flow cytometry are the rapid shedding of protein during flow cytometric manipulation of specimens, the high turnover rate of the molecule on the cell membrane, lack of cell surface antigen (Ag) in pre-apoptotic plasma cells or Ag expression dependent on stage of the cell cycle (Clement, 1995). By immunohistochemistry, CD138 has been reported to be highly sensitive and specific marker of MM cells in 100% of BM biopsies (Chilosi, 1999). These data support the potential value of CD138 as a target for immunotherapeutic approaches in MM.

Figure 2A:
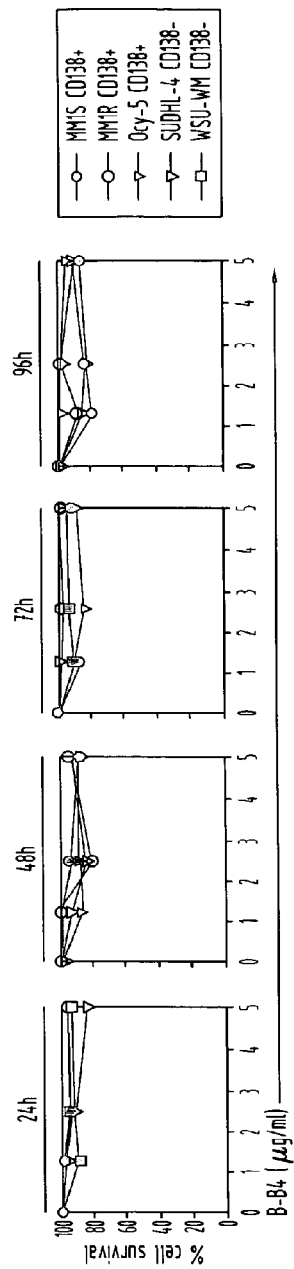
FIGS. 2A-2C show the effect of B-B4-DM1 in comparison with that produced by the naked antibody or by non-conjugated drug on survival of CD138$^+$ and CD138$^-$ MM cells.
Figure 2B:
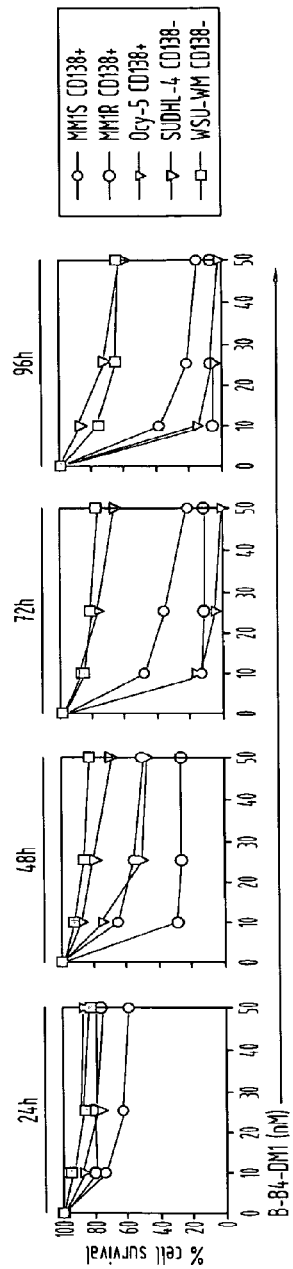
Figure 2C:
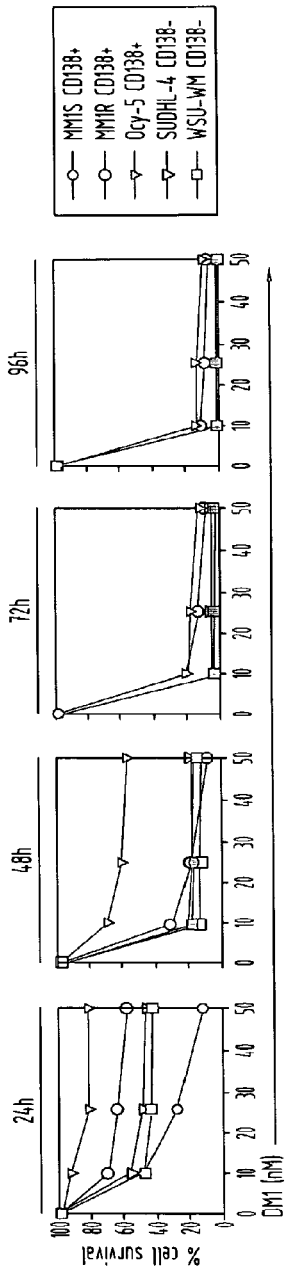

The effects of B-B4-DM1 on survival of CD138$^+$ (MM-1S, MM-1R, Ocy-My5) and CD138$^-$ cells (SUDHL-4 and WSU-WM) were determined using an MTT assay. MM cell lines were exposed to unconjugated B-B4 mAb (FIG. 2A), immunoconjugate B-B4-DM1 (FIG. 2B), or free DM1 drug at equimolar concentrations (FIG. 2C). Cell survival was measured using an MTT assay. Data (mean±SD of triplicate experiments) are shown in FIGS. 2A to 2C as percentage of untreated controls. CD138$^+$ MM cell lines MM-1S, MM-1R and Ocy-My5 were evaluated as well as CD138$^-$ cell lines including the lymphoma cell line SUDHL4 and the Waldestrom's Macroglobulinemia cell line WSU-WM.

As can be seen from FIG. 2B, treatment with B-B4-DM1 (1-50 nM) induced growth inhibition in CD138$^+$ tumor cells in a time- and dose-dependent manner. This effect was clearly detected after 72 h in all CD138$^+$ cells. B-B4-DM1 treatment of CD138$^+$ OPM1 and OPM2 MM cells further confirmed these observations (data not shown). In contrast, B-B4-DM1 (1-50 nM) was not toxic to CD138$^-$ cells, even after treatment for 96 h. To confirm that inhibitory activity of the immunoconjugate is specifically related to mAb-delivered cytotoxicity, the effect of equimolar concentrations of B-B4 antibody or unconjugated drug DM1 were tested. Even the highest concentrations of B-B4 did not affect the growth of cells at 96 h, (FIG. 2A), whereas free DM1 was equally and highly cytotoxic in both CD138+ and CD138− cell lines (FIG. 2C). These data indicate that activity of the immunoconjugate is not related to the differential sensitivity of cells to the drug nor the intrinsic properties of the antibody.

Since adhesion of MM cells to BMSC (bone marrow stromal cells) protects MM cells against drug-induced apoptosis, the effect of B-B4-DM1 on proliferation of CD138+ (Ocy-My5) MM and CD138− (SUDHL-4) LB cells adherent to BMSC was evaluated.

Figure 3A:
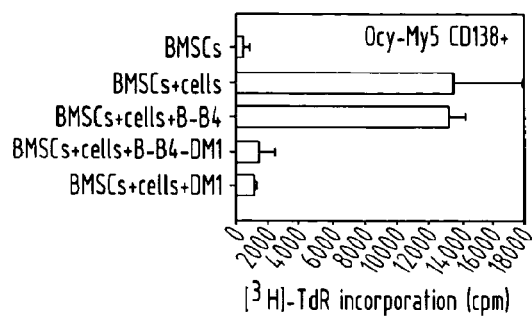
FIGS. 3A to 3C show the inhibitory effect of B-B4-DM1 on proliferation of CD138$^+$ and CD138$^-$ cells adherent to bone marrow stromal cells (BMSCs).
Figure 3B:
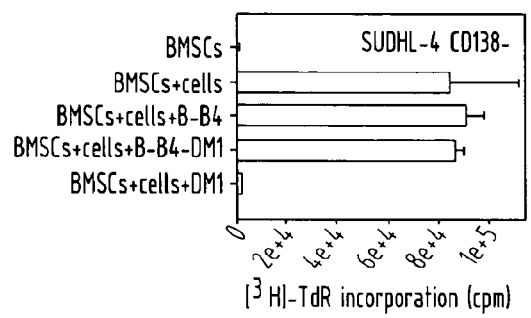

Ocy-My5 (FIG. 3A) or SUDHL-4 (FIG. 3B) cells ($2\times10^4$) were seeded on 70%-80% confluent BMSC for 24 h. Cell proliferation was measured by [$^3$H]thymidine incorporation following 72 h treatment with B-B4-DM1 (10 nM). Values represent the mean [$^3$H]-TdR incorporation (cpm) of triplicate cultures. As seen in FIGS. 3A and 3B, B-B4-DM1 (10 nM) significantly inhibited the proliferation of CD138+ Ocy-My5 cells, but had no significant effect on CD138− SUDHL-4 cells. Unconjugated B-B4 did not exert any significant effect, whereas free DM1 (10 nM) was cytotoxic to both cell lines.

Figure 3C:
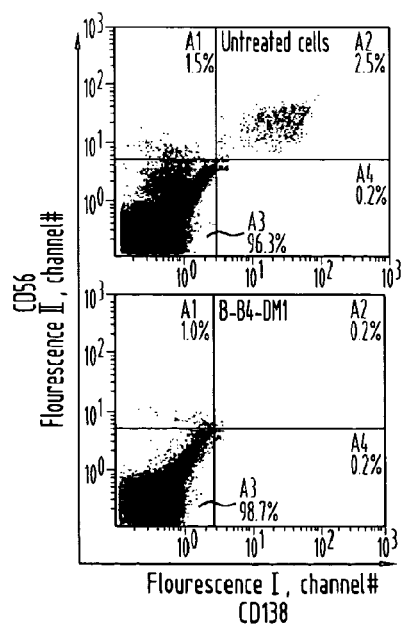

CD56, another CD associated with MM, and CD138 expression was evaluated by flow cytometry. Previous experiments established that B-B4-DM1, even at a concentrations as high as 240 μM, did not affect binding of FITC-labeled anti-CD138 antibody to CD138-expressing cells. FIG. 3C shows the cytotoxic activity of B-B4-DM1 (10 nM) on CD138+/CD56+ patient MM cells cultured with BMSCs using flow cytometry. Following 72 h of treatment with the immunoconjugate, >90% reduction in the MM cells was observed. Taken together, these results indicate that B-B4-DM1 overcomes cell adhesion mediated drug resistance (CAM-DR).

To determine whether apoptotic cell death occurs in cells exposed to the immunoconjugate, CD138+ Ocy-My5 MM cells were incubated with B-B4-DM1 (10 nM) for 72 h. Apoptotic cell death was then measured by staining with annexin V and PI and flow cytometric analysis.

Figure 4A:
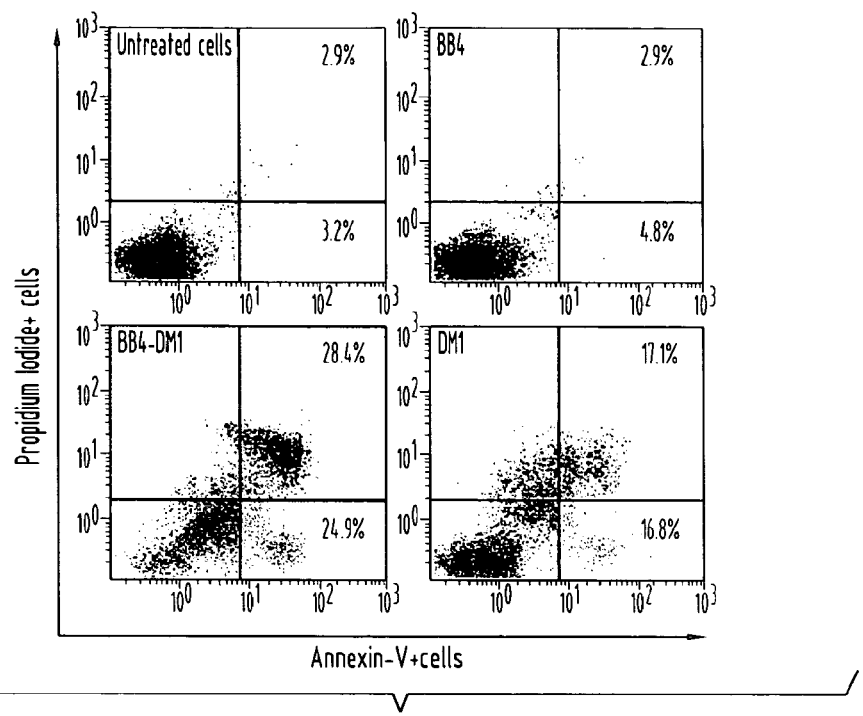
FIGS. 4A and 4B show the survival and cell cycle effects of B-B4-DM1 on CD138$^+$ MM cells.
Figure 4B:
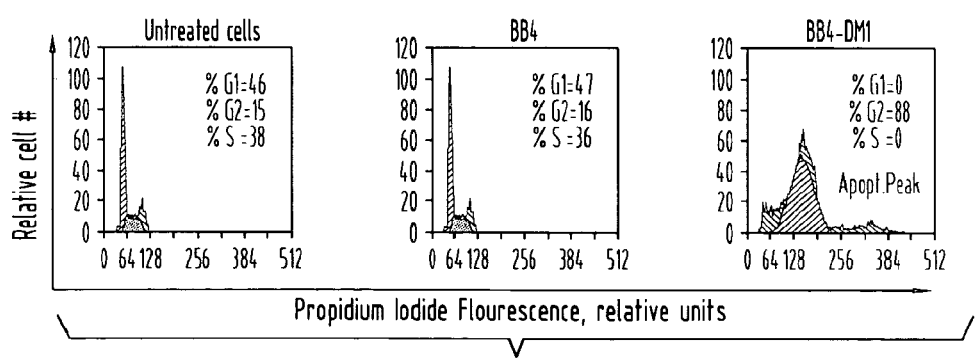

FIG. 4A shows the induction of apoptotic cell death in CD138+ Ocy-My5 MM cells after 48 h exposure to B-B4-DM1 (10 nM). Percentages of stained cells are reported in each quadrant. FIG. 4A shows a significant increase in both annexin V+/PI− and annexin V+/PI+ fractions in CD138+ cells exposed to B-B4-DM1 and free DM1, whereas no significant differences were detected in cells treated with unconjugated mAb alone. FIG. 4B shows the effects of B-B4-DM1 treatment on the cell cycle. Ocy-My5 MM cells were exposed to B-B4 mAb (13.3 μg/ml) or B-B4-DM1 (10 nM) for 48 h, labeled with PI, and analyzed using flow cytometry. Percentages of cells in the S-phase (S) and G2/M phase (G2) are indicated. As shown in FIG. 4B, B-B4 mAb alone had no significant effect on the proportion of cells in G2/M phase compared to untreated cells (15% vs 16%), whereas exposure of MM cells to B-B4-DM1 induced a majority (88%) of cells into the G2/M phase.

A human MM s.c. xenograft model in SCID mice was used to study the in vivo activity of B-B4-DM1 against CD138+ OPM1 cells. In this model, the therapeutic efficacy of B-B4-DM1 was measured in mice bearing large palpable tumors (average size 453±74 mm$^3$). Animals were treated daily i.v. for 3 consecutive days with vehicle alone (PBS 9phosphate buffered saline); n=5), unconjugated B-B4 (13.3 μg/ml; n=5), B-B4-DM1 (150 μg DM1/kg; n=5), or control huC242-DM1 (150 μg DM1/kg; n=5) which does not bind OPM1 cells. Tumor size and overall survival were monitored serially in this cohorts.

FIG. 5 shows the results obtained after CB-17 SCID mice were inoculated s.c. in the interscapular area with $5\times10^6$ OPM1 (A and B) or OPM2 (C and D) MM cells. Mice were treated i.v. with B-B4-DM1 or control mAbs for 3 consecutive days. Tumor volume was assessed in two dimensions using an caliper electronic, and the volume was expressed in mm$^3$ using the formula: V=0.5a×b$^2$, where a and b are the long and short diameter of the tumor, respectively. Tumor volume and survival were calculated as described previously.

Figure 5A:
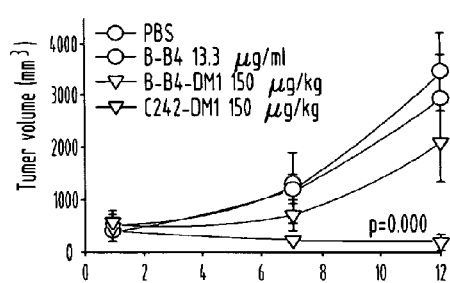
FIGS. 5A to 5D show the activity of B-B4-DM1 in a tumor xenograft model of human CD138$^+$ multiple myeloma.
Figure 5C:
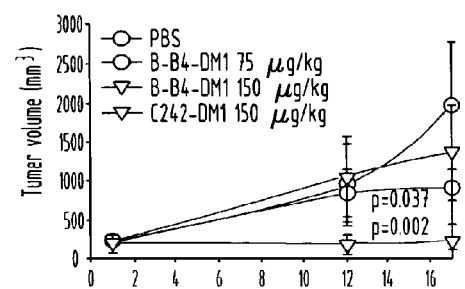
Figure 5B:
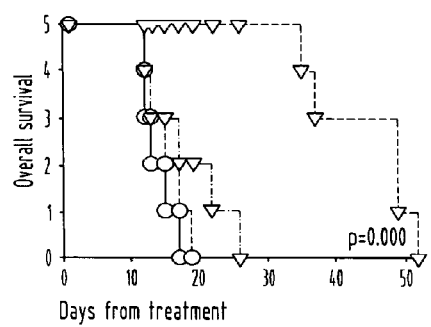
Figure 5D:
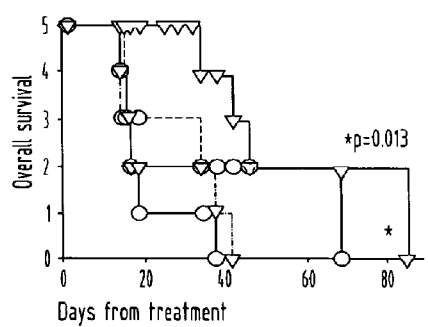

As shown in FIGS. 5A and 5B, vehicle alone, unconjugated B-B4 and huC242-DM1, had no significant effect on tumor growth (panel A) or survival (panel B). Importantly, treatment with 150 μg/kg of B-B4-DM1 induced tumor regression and a significant increase in survival (p<0.001). We also studied the effect induced by B-B4-DM1 (75 or 150 μg DM1/kg; n=10) against OPM2 MM cells. As shown in FIGS. 5C and D, treatment with 75 μg/kg of B-B4-DM1 induced a significant delay in tumor growth, and 150 μg/kg of B-B4-DM1 completely inhibited tumor growth. A significant increase in survival was also observed in mice treated at both dose levels (p<0.05) relative to animals treated with vehicle or huC242-DM1 alone. To confirm the activity of B-B4-DM1 (150 μg DM1/kg), animals bearing a significant burden of disease (average tumor size was 1309±60 mm$^3$) were treated. FIGS. 6A to 6F also shows the results obtained when CB-17 SCID mice were inoculated s.c. in the interscapular area with $5\times10^6$ OPM1 MM cells. Again, mice were treated iv. with B-B4-DM1 (150 μg DM1/kg) for a total of 3 consecutive days. Tumor volume was measured in two dimensions using a caliper, and the volume was expressed in mm$^3$ using the formula: V=0.5a×b$^2$, where a and b are the long and short diameter of the tumor, respectively.

As shown in FIGS. 6A to 6F, significant tumor regression was induced by B-B4-DM1 treatment. Taken together, these results indicate that B-B4-DM1 is highly active in controlling tumor growth in a murine xenograft model of human MM.

Figure 7A:
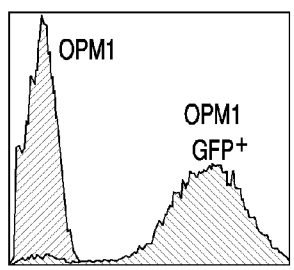
FIG. 7A shows the expression of GFP in the cells (GFP stands for Green Fluorescent Protein).
Figure 7B:
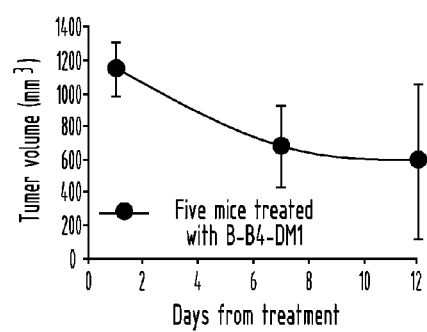
FIGS. 7B to 7F show the activity of B-B4-DM1 on GFP$^+$ human MM xenografts.
Figure 7C:
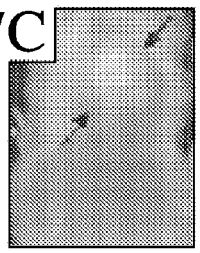
Figure 7D:
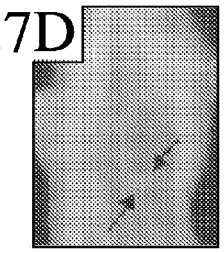
Figure 7E:
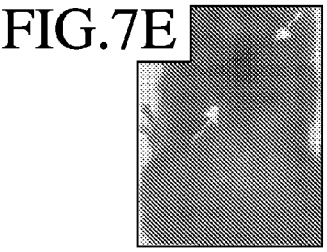
Figure 7F:
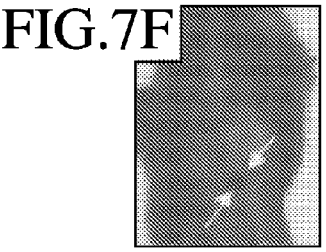

Since expression of reporter genes encoding fluorescent proteins are sensitive method for in vivo detection of localized tumor growth as well as distant metastasis, the OPM1 MM cells were transfected with green fluorescent protein (GFP) and B-B4-DM1 activity was further characterized. In particular, mice were injected s.c. with GFP+ OPM1 cells, followed by serial whole-body fluorescence imaging to assess development of GFP+ tumors. Mice were then treated with B-B4-DM1 (150 μg DM1/kg; n=5). FIG. 7A shows a flow cytometry analysis of GFP+ OPM1 cells, indicating a ~2-log difference in MFI of transfected cells. FIG. 7B shows results from five animals being injected with $5\times10^6$ GFP+ cells, monitored with whole-body fluorescence imaging for tumor development, and then treated with B-B4-DM1 (150 μg DM1/kg). Tumor sizes were determined directly by imaging the GFP-expressing tumor. FIGS. 7C and D are representative whole-body fluorescence imaging from a mouse treated with B-B4-DM1. FIGS. 7E and 7F are negative images of the representative mouse. As seen in FIGS. 7B and 7C to 7F, B-B4-DM1 induced significant regressions of GFP+ tumors, confirming high activity of the immunoconjugate against CD138+ MM cells.

Since the SCID-hu model of MM accurately reproduces the pathological behaviours of the disease, the efficacy of B-B4-DM1 treatment was tested in (i) SCID-hu mice injected with patient MM cells and (ii) SCID-hu mice injected with Ocy-My5 MM cell line (Urashima, 1997). The activity of the immunoconjugate on disease confined to the human fetal bone chip implanted s.c. in mice was studied. Four mice with patient MM cells growing in human bone environment increasing serum huIg levels, were treated with either B-B4-DM1 (150 μg DM1/kg) or the control huC242-DM1 (150 μg DM1/kg).

Figure 8A:
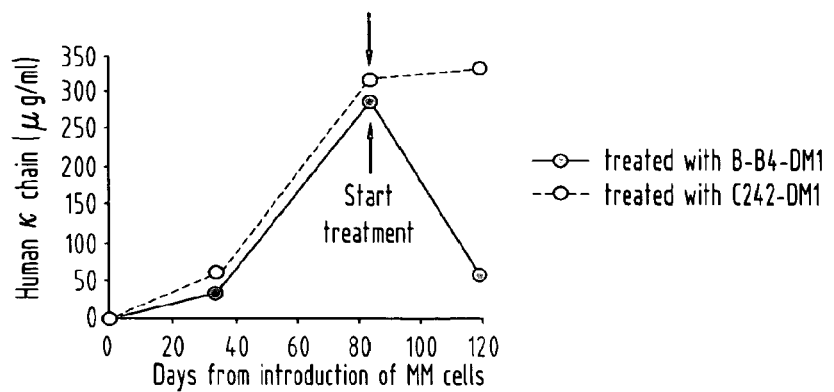
FIGS. 8A to 8C show that B-B4-DM1 reduces MM tumor burden in SCID-hu hosts implanted with patient MM cells.
Figure 8B:
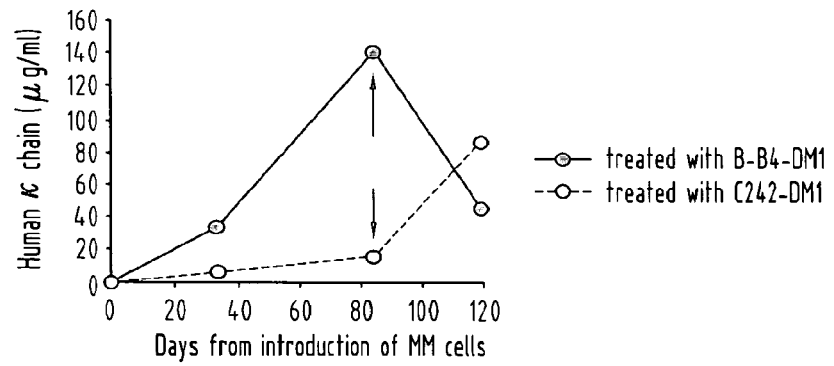
Figure 8C:
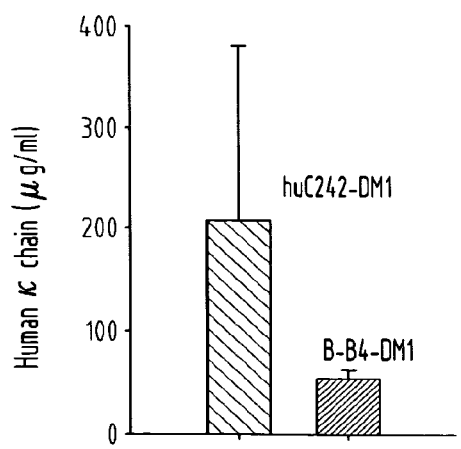

In FIGS. 8A and 8B the results of monitoring mice for changes in levels of human κ chain as an indicator of disease burden are shown. The Figure shows a significant reduction of κ levels after treatment with B-B4-DM1. FIG. 8C shows final human κ chain levels (mean±SD) (n=4) after treatment. As seen in FIGS. 8A to 8C, treatment with B-B4-DM1 induced a significant reduction of human paraprotein, whereas human paraprotein continued to rise in mice treated with control antibody.

Figure 9A:
FIGS. 9A to 9C show that B-B4-DM1 increases survival in SCID-hu hosts implanted with the Ocy-My5 MM cell line.
Figure 9B:
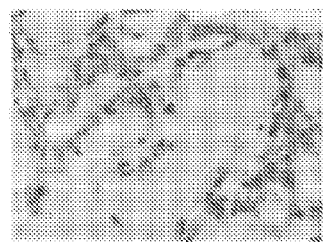
Figure 9C:
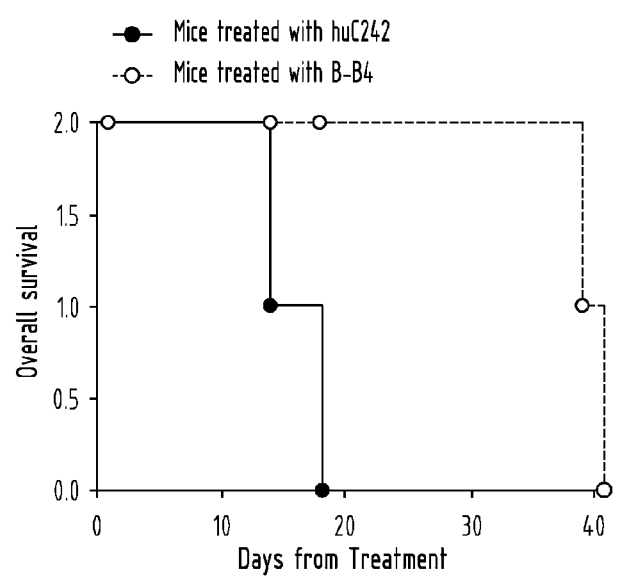

The activity of B-B4-DM1 after injection of Ocy-My5 cells in human fetal bone, tumor cell growth in bone (FIGS. 9A and 9B) and subsequent spread to surrounding tissues was also studied (Urashima, 1997) were treated with either B-B4-DM1 (150 μg DM1/kg) or the control huC242-DM1 (150 μg DM1/kg). FIGS. 9A and 9B show representative human bone sections after implantation of Ocy-My5 cells and before treatment. Sections are respectively stained by H & E and with anti-λ mAb. Finally, the activity of B-B4-DM1 on survival of tumor bearing mice was studied. FIG. 9C shows the survival of mice measured from the first day of treatment to the day of death or sacrifice. Figure shows a significant prolongation of survival after treatment with B-B4-DM1 As seen in FIG. 9C, treatment with B-B4-DM1 (150 μg DM1/kg) induced a significant prolongation in survival compared with control huC242-DM1 (150 μg DM1/kg) therapy. Taken together, these results confirm in vivo B-B4-DM1 activity in preclinical models which mimic many features of human MM.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

REFERENCES

Akkina R K, Rosenblatt J D, Campbell A G, Chen I S, Zack J A. Modeling human lymphoid precursor cell gene therapy in the SCID-hu mouse. Blood. 1994; 84:1393-1398.

Anttonen A, Heikkila P, Kajanti M, Jalkanen M, Joensuu H. High syndecan-1 expression is associated with favourable outcome in squamous cell lung carcinoma treated with radical surgery. Lung Cancer. 2001 June; 32(3):297-305.

Barbareschi M, Maisonneuve P, Aldovini D, Cangi M G, Pecciarini L, Angelo Mauri F, Veronese S, Caffo O, Lucenti A, Palma P D, Galligioni E, Doglioni C. High syndecan-1 expression in breast carcinoma is related to an aggressive phenotype and to poorer prognosis. Cancer. 2003 Aug. 1; 98(3):474-83.

Bernfield M, Kokenyesi R, Kato M, Hinkes M T, Spring J, Gallo R L, Lose E J. Biology of the syndecans: a family of transmembrane heparan sulfate proteoglycans. Annu Rev Cell Biol. 1992; 8:365-393.

Beste G, Schmidt F S, Stibora T, Skerra A. Small antibody-like proteins with prescribed ligand specificities derived from the lipocalin fold. Proc. Natl. Acad. Sci. USA. 1999: 96, 1898-1903.

Bhattacharyya B, Wolff J. Maytansine binding to the vinblastine sites of tubulin. FEBS Lett. 1977; 75:159-162.

Blättler W A and Chari R V J. Drugs to Enhance the Therapeutic Potency of Anticancer Antibodies: Antibody-Drug Conjugates as Tumor-Activated Prodrugs. In: Ojima, I., Vite, G. D. and Altmann, K.-H., Editors, 2001. Anticancer Agents-Frontiers in Cancer Chemotherapy, American Chemical Society, Washington, D.C., pp. 317-338.

Bross P F, Beitz J, Chen G, Chen X H, Duffy E, Kieffer L, Roy S, Sridhara R, Rahman A, Williams G, Pazdur R. Approval summary: gemtuzumab ozogamicin in relapsed acute myeloid leukemia. Clin Cancer Res. 2001; 7:1490-1496.

Carbone A, Gaidano G, Gloghini A, Ferlito A, Rinaldo A, Stein H. AIDS-related plasma-blastic lymphomas of the oral cavity and jaws: a diagnostic dilemma. Ann. Otol. Rhinol. Laryngol. 1999; 108: 95-99.

Carter P. Improving the efficacy of antibody-based cancer therapies. Nat Rev Cancer. 2001; 1:118-129.

Chari R V, Martell B A, Gross J L, Cook S B, Shah S A, Blattler W A, McKenzie S J, Goldmacher V S. Immunoconjugates containing novel maytansinoids: promising anticancer drugs. Cancer Res. 1992; 52:127-131.

Chari R V, Jackel K A, Bourret L A, Derr S M, Tadayoni B M, Mattocks K M, Shah S A, Liu C, Blattler W A and Goldmacher V S. Enhancement of the selectivity and antitumor efficacy of a CC-1065 analogue through immunoconjugate formation. Cancer Res. 1995; 55: 4079-4084.

Charnaux N, Brule S, Chaigneau T, Saffar L, Sutton A, Hamon M, Prost C, Lievre N, Vita C, Gattegno L. RANTES (CCL5) induces a CCR5-dependent accelerated shedding of syndecan-1 (CD138) and syndecan-4 from HeLa cells and forms complexes with the shed ectodomains of these proteoglycans as well as with those of CD44. Glycobiology. 2004 Sep. 8 [Epub ahead of print]

Chen B P, Galy A, Kyoizumi S, Namikawa R, Scarborough J, Webb S, Ford B, Cen D Z, Chen S C. Engraftment of human hematopoietic precursor cells with secondary transfer potential in SCID-hu mice. Blood. 1994; 84:2497-2505.

Chilosi M, Adami F, Lestani M, Montagna L, Cimarosto L, Semenzato G, Pizzolo G, Menestrina F. CD138/syndecan-1: a useful immunohistochemical marker of normal and neoplastic plasma cells on routine trephine bone marrow biopsies. Mod Pathol. 1999; 12:1101-1106.

Clement C, Vooijs, W. C., Klein, B., and Wijdenes, J. In: al. SFSe, ed. J. Leukocyte Typing V. Oxford: Oxford University Press; 1995:714-715.

Couturier O, Faivre-Chauvet A; Filippovich I V; Thedréz P, Saï-Maurel C; Bardiés M; Mishra A K; Gauvrit M; Blain G; Apostolidis C; Molinet R; Abbe J C; Bateille R; Wijdenes J; Chatal J F; Cherel M; Validation of 213Bi-alpha radioimmunotherapy for multiple myeloma. Clinical Cancer Research 5(10 Suppl.) (October 1999) 3165s-3170s.

Davies E J et al., Blackhall F H, Shanks J H, David G, McGown A T, Swindell R, Slade R J, Martin-Hirsch P, Gallagher J T, Jayson G C. Distribution and Clinical Significance of Heparan Sulfate Proteoglycans in Ovarian Cancer Clin Cancer Res. 2004; 10(15):5178-86.

Dhodapkar M V, Abe E, Theus A, Lacy M, Langford J K, Barlogie B, Sanderson R D. Syndecan-1 is a multifunctional regulator of myeloma pathobiology: control of tumor cell survival, growth, and bone cell differentiation. Blood. 1998; 91:2679-2688.

Dore J M, Morard F, Vita N, Wijdenes J. Identification and location on syndecan-1 core protein of the epitopes of B-B2 and B-B4 monoclonal antibodies. FEBS Lett. 1998; 426:67-70.

Dowell J A, Korth-Bradley J, Liu H, King S P, Berger M S. Pharmacokinetics of gemtuzumab ozogamicin, an antibody-targeted chemotherapy agent for the treatment of patients with acute myeloid leukemia in first relapse. J Clin Pharmacol. 2001; 41:1206-1214.

Edinger M, Sweeney T J, Tucker A A, Olomu A B, Negrin R S, Contag C H. Noninvasive assessment of tumor cell proliferation in animal models. Neoplasia. 1999; 1:303-310.

Gattei V, Godeas C, Degan M, Rossi F M, Aldinucci D, Pinto A. Characterization of Anti-CD138 monoclonal antibodies as tools for investigating the molecular polymorphism of syndecan-1 in human lymphoma cells. Br J. Haematol. 1999; 104:152-162.

Hamann P R, Hinman L M, Beyer C F, Lindh D, Upeslacis J, Flowers D A, Bernstein I. An anti-CD33 antibody-calicheamicin conjugate for treatment of acute myeloid leukemia. Choice of linker. Bioconjug Chem. 2002; 13:40-46.

Han I, Park H, Oh E S. New insights into syndecan-2 expression and tumourigenic activity in colon carcinoma cells. J Mol. Histol. 2004: 35(3):319-26.

Horvathova M, Gaillard, J.-P., Liutard, J., Duperray, C., Lavabre-Bertrand, T., Bourquard, P et al. In: al. SFSe, ed. Leucocyte Typing V. Oxford: Oxford University Press; 1995:713-714.

Krebs B, Rauchenberger R, Reiffert S, Rothe C, Tesar M, Thomassen E, Cao M, Dreier T, Fischer D, Hoss A et al. High-throughput generation and engineering of recombinant human antibodies. 2001. J. Immunol. Methods 254, pp. 67-84.

Kupchan S M, Sneden A T, Branfman A R, Howie G A, Rebhun L I, Mclvor W E, Wang R W, Schnaitman T C. Structural requirements for antileukemic activity among the naturally occurring and semisynthetic maytansinoids. J Med Chem. 1978; 21:31-37.

Kyoizumi S, Baum C M, Kaneshima H, McCune J M, Yee E J, Namikawa R. Implantation and maintenance of functional human bone marrow in SCID-hu mice. Blood. 1992; 79:1704-1711.

Kyoizumi S, Murray L J, Namikawa R. Preclinical analysis of cytokine therapy in the SCID-hu mouse. Blood. 1993; 81:1479-1488.

Liu C, Tadayoni B M, Bourret L A, Mattocks K M, Derr S M, Widdison W C, Kedersha N L, Ariniello P D, Goldmacher V S, Lambert J M, Blattler W A, Chari R V. Eradication of large colon tumor xenografts by targeted delivery of maytansinoids. Proc Natl Acad Sci USA. 1996; 93:8618-8623.

McCune J M, Namikawa R, Kaneshima H, Shultz L D, Lieberman M, Weissman I L. The SCID-hu mouse: murine model for the analysis of human hematolymphoid differentiation and function. Science. 1988; 241:1632-1639.

Mennerich D, Vogel A, Klaman I, Dahl E, Lichtner R B, Rosenthal A, Pohlenz H D, Thierauch K H, Sommer A. Shift of syndecan-1 expression from epithelial to stromal cells during progression of solid tumours. Eur J Cancer. 2004 June; 40(9):1373-82.

Mosmann T. Rapid colorimetric assay for cellular growth and survival: application to proliferation and cytotoxicity assays. J Immunol Methods. 1983; 65:55-63. Namikawa R, Ueda R, Kyoizumi S. Growth of human myeloid leukemias in the human marrow environment of SCID-hu mice. Blood. 1993; 82:2526-2536.

O'Connell F P, Pinkus J L, Pinkus G S. CD138 (Syndecan-1), a Plasma Cell Marker Immunohistochemical Profile in Hematopoietic and Nonhematopoietic Neoplasms. Am J Clin Pathol 2004; 121:254-263.

Ojima I, Geng X, Wu X, Qu C, Borella C P, Xie H, Wilhelm S D, Leece B A, Bartle L M, Goldmacher V S and Chari R V. Tumor-specific novel taxoid-monoclonal antibody conjugates. 2002. J. Med. Chem. 45, pp. 5620-5623.

Olafsen, T, Cheung, C C, Yazaki, P J, Li L, Sundaresan G, Gambhir S S, Sherman, M A, Williams, L E, Shively, J E, Raubitschek, A A, and Wu, A M. Covalent disulfide-linked anti-CEA diabody allows site-specific conjugation and radiolabeling for tumor targeting applications. 2004; Prot. Eng. Design & Selection 17:1: 21-27.

Orosz Z, Kopper L. Syndecan-1 expression in different soft tissue tumours. Anticancer Res. 2001: 21 (1B):733-7.

Padlan, E A. A possible procedure for reducing the immunogenicity of antibody variable domains while preserving their ligand-binding properties. Mol. Immunol. 1991; 28: 489-498.

Payne G. Progress in immunoconjugate cancer therapeutics. Cancer Cell. 2003; 3:207-212.

Pegram M D, Lipton A, Hayes D F, Weber B L, Baselga J M, Tripathy D, Baly D, Baughman S A, Twaddell T, Glaspy J A and Slamon D J. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. 1998. J. Clin. Oncol. 16, pp. 2659-2671.

Rawstron A C, Owen R G, Davies F E, Johnson R J, Jones R A, Richards S J, Evans P A, Child J A, Smith G M, Jack A S, Morgan G J. Circulating plasma cells in multiple myeloma: characterization and correlation with disease stage. Br J. Haematol. 1997; 97:46-55.

Remillard S, Rebhun L I, Howie G A, Kupchan S M. Antimitotic activity of the potent tumor inhibitor maytansine. Science. 1975; 189:1002-1005.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994; 91:969-973.

Ross S, Spencer S D, Holcomb I, Tan C, Hongo J, Devaux B, Rangell L, Keller G A, Schow P, Steeves R M, Lutz R J, Frantz G, Hillan K, Peale F, Tobin P, Eberhard D, Rubin M A, Lasky L A, Koeppen H. Prostate stem cell antigen as therapy target: tissue expression and in vivo efficacy of an immunoconjugate. Cancer Res. 2002 May 1; 62(9):2546-53.

Ross J S, Gray K, Gray G, Worland P J, Rolfe M. Anticancer Antibodies, Am J Clin Path. (Apr. 17, 2003).

Sanderson R D, Lalor P, Bernfield M. B lymphocytes express and lose syndecan at specific stages of differentiation. Cell Regul. 1989; 1:27-35.

Sandhu J S, Clark B R, Boynton E L, Atkins H, Messner H, Keating A, Hozumi N. Human hematopoiesis in SCID mice implanted with human adult cancellous bone. Blood. 1996; 88:1973-1982.

Sasaki A, Boyce B F, Story B, Wright K R, Chapman M, Boyce R, Mundy G R, Yoneda T. Bisphosphonate risedronate reduces metastatic human breast cancer burden in bone in nude mice. Cancer Res. 1995; 55:3551-3557.

Schneider U, van Lessen A, Huhn D, Serke S. Two subsets of peripheral blood plasma cells defined by differential expression of CD45 antigen. Br J. Haematol. 1997; 97:56-64.

Sebestyen A, Berczi L, Mihalik R, Paku S, Matolcsy A, Kopper L. Syndecan-1 (CD138) expression in human non-Hodgkin lymphomas. Br J Haematol. 1999; 104(2):412-9.

Seftalioglu A, Karakus S. Syndecan-1/CD138 expression in normal myeloid, acute lymphoblastic and myeloblastic leukemia cells. Acta Histochem. 2003; 105:213-221.

Seftalioglu A, Karakus S, Dundar S, Can B, Erdemli E, Irmak M K, Oztas E, Korkmaz C, Yazar F, Cavusoglu I. Syndecan-1 (CD138) expression in acute myeloblastic leukemia cells—an immuno electron microscopic study. Acta Oncol. 2003; 42:71-74.

Senter P D, Doronina S, Cerveny C, Chace D, Francisco J, Klussman K, Mendelsohn B, Meyer D, Siegall C B, Thompson J et al. (2002). Cures and regressions of established tumors with monoclonal antibody auristatin conjugates. Abstract #2062, American Assoication for Cancer Res. (San Francisco, Calif.: American Association for Cancer Res.), 414.

Sievers E L, Larson R. A., Stadtmauer, E. A., Estey, E., Lowenberg, B., Dombret, H., Karanes, C., Theobald, M., Bennett, J. M., Sherman, M. L. et al. Efficacy and safety of gemtuzumab ozogamicin in patients with CD33-positive acute myeloid leukemia in first relapse. 2001. J. Clin. Oncol. 19, pp. 3244-3254.

Sievers E L and Linenberger M. Mylotarg: antibody-targeted chemotherapy comes of age. 2001. Curr. Opin. Oncol. 13, pp. 522-527.

Smith R., Single chain antibody variable region fragments; www.standford.edu/~smithr/science/scf.html (last updated on May, 2001).

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994: 7(6): 805-814.

Tolcher A W, Ochoa L, Hammond L A, Patnaik A, Edwards T, Takimoto C, Smith L, de Bono J, Schwartz G, Mays T, Jonak Z L, Johnson R, DeWitte M, Martino H, Audette C, Maes K, Chari R V, Lambert J M, Rowinsky E K. Cantuzumab mertansine, a maytansinoid immunoconjugate directed to the CanAg antigen: a phase I, pharmacokinetic, and biologic correlative study. J Clin Oncol. 2003; 21:211-222.

Urashima M, Chen B P, Chen S, Pinkus G S, Bronson R T, Dedera D A, Hoshi Y, Teoh G, Ogata A, Treon S P, Chauhan D, Anderson K C. The development of a model for the homing of multiple myeloma cells to human bone marrow. Blood. 1997; 90:754-765.

Vogel C W. Preparation of immunoconjugates using antibody oligosaccharide moieties. Methods in Molecular Biology: Bioconjugation protocols strategies and methods. 2004; 283:087-108.

Vooijs W C, Post J, Wijdenes J, Schuurman H J, Bolognesi A, Polito L, Stirpe F, Bast E J, de Gast G C. Efficacy and toxicity of plasma-cell-reactive monoclonal antibodies B-B2 and B-B4 and their immunotoxins. Cancer Immunol Immunother. 1996; 42:319-328.

Ward, E. S., D. Gussow, A. D. Griffiths, P. T. Jones, and G. Winter. Binding activities of a repertoire of single immunoglobin variable domains secreted from *Escherichia coli*. Nature. 1989. 341:544-546.

Wargalla U C, Reisfeld R A. Rate of internalization of an immunotoxin correlates with cytotoxic activity against human tumor cells. Proc. Natl. Acad. Sci. USA. 1989; 86:5146-5150.

Wijdenes J, Vooijs W C, Clement C, Post J, Morard F, Vita N, Laurent P, Sun R X, Klein B, Dore J M. A plasmocyte selective monoclonal antibody (B-B4) recognizes syndecan-1. Br J. Haematol. 1996; 94:318-323.

Wijdenes J, Dore J M, Clement C, Vermot-Desroches C. CD138, J Biol Regul Homeost Agents. 2002 April-June; 16(2):152-5.

Witzig T E, Kimlinger T K, Ahmann G J, Katzmann J A, Greipp P R. Detection of myeloma cells in the peripheral blood by flow cytometry. Cytometry. 1996; 26:113-120.

Xie H, Audette C, Hoffee M, Lambert J M, Blattler W. Pharmacokinetics and biodistribution of the antitumor immunoconjugate, cantuzumab mertansine (huC242-DM1), and its two components in mice. J Pharmacol Exp Ther. 2004 March;308(3):1073-82.

Yang M, Jiang P, An Z, Baranov E, Li L, Hasegawa S, Al-Tuwaijri M, Chishima T, Shimada H, Moossa A R, Hoffman R M. Genetically fluorescent melanoma bone and organ metastasis models. Clin Cancer Res. 1999; 5:3549-3559.

Yang M, Baranov E, Jiang P, Sun F X, Li X M, Li L, Hasegawa S, Bouvet M, Al-Tuwaijri M, Chishima T, Shimada H, Moossa A R, Penman S, Hoffman R M. Whole-body optical imaging of green fluorescent protein-expressing tumors and metastases. Proc Natl Acad Sci USA. 2000; 97:1206-1211.

What is claimed is:

1. A method for treating a patient having CD138 expressing tumor cells comprising
   administering to said patient at least one immunoconjugate in therapeutically effective amount,
   wherein said immunoconjugate comprises at least one effector molecule, wherein said effector molecule is a maytansinoid and has a molecular weight of less than 2 kDa and at least one targeting antibody selectively targeting cell-surface expressed CD138, wherein the targeting antibody binds to a linear epitope between residues 90-95 of the core protein on human CD138, and
   wherein said immunoconjugate delivers said effector molecule to said CD138 expressing tumor cells and said effector molecule is released.

2. The method of claim 1, wherein said patient suffers from an hematologic malignancy and/or a solid tumor comprising CD138 expressing cells.

3. The method of claim 2, wherein said patient suffers from one of the following: multiple myeloma, ovarian carcinoma, kidney carcinoma, gall bladder carcinoma, breast carcinoma, prostate cancer, lung cancer, colon carcinoma, Hodgkin's and non-Hodgkin's lymphoma, chronic lymphocytic leukemia (CLL), acute lymphoblastic leukemia (ALL), acute myeloblastic leukemia (AML), solid tissue sarcoma or colon carcinoma.

4. The method of claim 3, wherein the disease is multiple myeloma.

5. The method of claim 1, wherein said effector molecule exhibits, in its native form, high non-selective cytotoxicity.

6. The method of claim 1, wherein said maytansinoid has a molecular weight between about 600 Da and about 800 Da.

7. The method of claim 6, wherein the maytansinoid has, in its native form, a potency of about $10^{-11}$ to $10^{-8}$.

8. The method of claim 1, wherein said maytansinoid is DM1 or DM4.

9. A method for treating a patient having CD138 expressing myeloma cells comprising:
   administering to said patient at least one immunoconjugate in a therapeutically effective amount, wherein said immunoconjugate comprises at least one effector molecule, wherein said effector molecule has a molecular weight of less than 2 kDa and at least one targeting antibody selectively targeting cell-surface expressed CD138, wherein the targeting antibody binds to a linear epitope between residues 90-95 of the core protein on human CD138; and
   wherein said immunoconjugate delivers said effector molecule to said CD138 expressing myeloma cells and said at least one effector molecule is released.

10. The method of claim 9, wherein the immunoconjugate comprises a targeting antibody derived from antibody B-B4.

\* \* \* \* \*